US012178897B2

(12) United States Patent
Abbas et al.

(10) Patent No.: US 12,178,897 B2
(45) Date of Patent: Dec. 31, 2024

(54) OXIDATIVE DYEING AGENT FOR KERATIN FIBERS COMPRISING NOVEL DYE PRECURSOR COMBINATIONS

(71) Applicant: Henkel AG & Co. KGaA, Duesseldorf (DE)

(72) Inventors: Razi Abbas, Shelton, CT (US); Tugce Cansev, Hamburg (DE); Thomas Hippe, Appen (DE); Astrid Kleen, Haseldorf (DE); Hartmut Manneck, Barnitz (DE); Stefan Hoepfner, Hamburg (DE); Tiffany Lea Fielder, Norwalk, CT (US)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 18/111,365

(22) Filed: Feb. 17, 2023

(65) Prior Publication Data
US 2023/0270649 A1 Aug. 31, 2023

Related U.S. Application Data

(60) Provisional application No. 63/314,237, filed on Feb. 25, 2022.

(51) Int. Cl.
*A61Q 5/10* (2006.01)
*A61K 8/20* (2006.01)
*A61K 8/22* (2006.01)
*A61K 8/34* (2006.01)
*A61K 8/41* (2006.01)
*A61K 8/46* (2006.01)
*A61K 8/49* (2006.01)
*A61K 8/81* (2006.01)

(52) U.S. Cl.
CPC .............. *A61K 8/4973* (2013.01); *A61K 8/20* (2013.01); *A61K 8/22* (2013.01); *A61K 8/345* (2013.01); *A61K 8/411* (2013.01); *A61K 8/415* (2013.01); *A61K 8/463* (2013.01); *A61K 8/4926* (2013.01); *A61K 8/494* (2013.01); *A61K 8/8158* (2013.01); *A61Q 5/10* (2013.01); *A61K 2800/30* (2013.01); *A61K 2800/882* (2013.01)

(58) Field of Classification Search
CPC .......... A61K 8/4973; A61K 8/20; A61K 8/22; A61K 8/345; A61K 8/411; A61K 8/415; A61K 8/463; A61K 8/4926; A61K 8/494; A61K 8/8158; A61K 2800/30; A61K 2800/882; A61K 8/498; A61K 8/347; A61Q 5/10
See application file for complete search history.

(56) References Cited

U.S. PATENT DOCUMENTS

| | | | |
|---|---|---|---|
| 4,395,262 A | 7/1983 | Konrad et al. | |
| 2003/0131423 A1 | 7/2003 | Javet et al. | |
| 2003/0145764 A1 | 8/2003 | Chassot | |
| 2004/0187226 A1 | 9/2004 | Muerner et al. | |
| 2004/0237218 A1* | 12/2004 | Marsh | A61Q 5/10 8/405 |
| 2005/0005370 A1 | 1/2005 | Lim et al. | |
| 2005/0188480 A1 | 9/2005 | Lim et al. | |
| 2009/0056039 A1 | 3/2009 | Schmenger et al. | |
| 2011/0067723 A1* | 3/2011 | Bureiko | A61K 8/556 8/406 |
| 2015/0259625 A1 | 9/2015 | Bureiko et al. | |
| 2017/0158608 A1* | 6/2017 | Murphy | C07C 213/02 |
| 2017/0165173 A1* | 6/2017 | Flohr | A61K 8/415 |
| 2020/0375865 A1 | 12/2020 | Wang | |
| 2021/0177717 A1 | 6/2021 | Consoli et al. | |
| 2023/0390174 A1 | 12/2023 | Paillard-Brunet et al. | |
| 2024/0065955 A1 | 2/2024 | Nicou et al. | |
| 2024/0115479 A1 | 4/2024 | Nicou | |

FOREIGN PATENT DOCUMENTS

| | | |
|---|---|---|
| CA | 2576189 A1 | 6/2007 |
| CA | 2646866 A1 | 3/2009 |
| CN | 105596228 A | 5/2016 |
| DE | 3028202 A1 | 2/1982 |
| DE | 29909427 U1 | 7/1999 |
| DE | 29912882 U1 | 9/1999 |
| DE | 20107481 U1 | 8/2001 |
| DE | 20118089 U1 | 1/2002 |
| EP | 727203 A1 | 8/1996 |
| EP | 1103542 A2 | 5/2001 |
| EP | 1166748 A2 | 1/2002 |
| EP | 3287120 A1 | 2/2018 |
| FR | 2988591 A1 | 10/2013 |
| FR | 3026007 A1 | 3/2016 |
| GB | 2239265 A | 6/1991 |
| IN | 202041012228 A | 9/2021 |

(Continued)

OTHER PUBLICATIONS

Application No. PCT/US2023/013298 International Search Report Completed Jun. 7, 2023; Mailed: Jun. 8, 2023 14 pgs.
Application No. PCT/US2023/013317 International Search Report Completed Jun. 7, 2023; Mailed 6/8/02023 13 pgs.
Application No. PCT/US2023/013332 International Search Report Completed Jun. 13, 2023; Mailed Jun. 14, 2023 13 pgs.
Application No. PCT/US2023/013341 International Search Report Completed Jun. 15, 2023; Mailed Jun. 15, 2023 12 pgs.
Lubrizol. "Hair Care / Conditioning Polymers Differentiation Chart". 2017. Lubrizol Advanced Materials Inc. www.lubrizol.com/personalcare.

(Continued)

*Primary Examiner* — Eisa B Elhilo
(74) *Attorney, Agent, or Firm* — P. Scott Smith

(57) ABSTRACT

The subject of the present application is an agent for the oxidative dyeing of keratinous fibers, in particular human hair, which contains the coupling oxidation dye precursors 2-(1,3-benzodioxol-5-ylamino)ethanol and 1-phenyl-3-methylpyrazol-5-one in combination with at least one oxidation base.

17 Claims, No Drawings

(56) References Cited

FOREIGN PATENT DOCUMENTS

| JP | 2001055316 A  | 2/2001  |
|----|---------------|---------|
| WO | 2005072688 A1 | 8/2005  |
| WO | 2013049575 A2 | 4/2013  |
| WO | 2014202713 A1 | 12/2014 |
| WO | 2019125788 A1 | 6/2019  |
| WO | 2020258731 A1 | 12/2020 |
| WO | 2021083904 A1 | 5/2021  |
| WO | 2021084085 A1 | 5/2021  |
| WO | 2023105016 A1 | 6/2023  |
| WO | 2023105019 A1 | 6/2023  |
| WO | 2023105021 A1 | 6/2023  |
| WO | 2023105025 A1 | 6/2023  |

OTHER PUBLICATIONS

Scientific Committee on Consumer Safety (SCCS). "Opinion on Hydroxyethyl-3,4-methylenedioxyaniline HCI, Colipa n° A98". Dec. 8, 2009. SCCS/1269/09. https://ec.europa.eu/health/scientific_committees/consumer_safety/docs/sccs_o_006.pdf.

Scientific Committee on Consumer Safety (SCCS). "Opinion on 2-Methoxy-methyl-p-phenylenediamine and its sulfate salt, Colipa n° A160". Dec. 26, 2013. SCCS/1491/12. https://ec.europa.eu/health/scientific_committees/consumer_safety/docs/sccs_o_123.pdf.

Scientific Committee on Consumer Products (SCCP). "Opinion on Phenyl Methyl Pyrazolone, Colipa n° A39". Dec. 19, 2006. SCCP/1033/06. https://ec.europa.eu/health/ph_risk/committees/04_sccp/docs/sccp_o_087.pdf.

Scientific Committee on Consumer Products (SCCP). "Opinion on 4-Amino-2-hydroxytoluene, Colipa n° A27". Oct. 10, 2006. SCCP/1001/06. https://ec.europa.eu/health/ph_risk/committees/04_sccp/docs/sccp_o_070.pdf.

Scientific Committee on Consumer Products (SCCP). "Opinion on 1-Hydroxyethyl-4,5-Diamino Pyrazole Sulfate, Colipa n° A154". Jun. 20, 2006. SCCP/0990/06. https://ec.europa.eu/health/ph_risk/committees/04_sccp/docs/sccp_o_064.pdf.

Scientific Committee on Consumer Products (SCCP). "Opinion on 2-Methylmethyl-5-Hydroxyethylaminophenol, Colipa n° A31". Mar. 28, 2006. SCCP/0957/05. https://ec.europa.eu/health/ph_risk/committees/04_sccp/docs/sccp_o_040.pdf.

Scientific Committee on Consumer Products (SCCP). "Opinion on M-Aminophenol, Colipa n° A15". Dec. 19, 2006. SCCP/0978/06. https://ec.europa.eu/health/ph_risk/committees/04_sccp/docs/sccp_o_088.pdf.

Scientific Committee on Consumer Safety (SCCS). "Opinion on 2,4-Diaminophenoxyethanol dihydrochloride and sulfate, Colipa n° A42". Sep. 21, 2010. SCCS/1367/10. https://health.ec.europa.eu/document/download/86a2e0d7-3175-4f5f-a7a4-b0e9df0dc173_en?filename=sccs_o_035.pdf.

Scientific Committee on Consumer Products (SCCP). "Opinion on 1,3-bis-(2,4-Diaminophenoxy)propane, Colipa n° A79". Jun. 19, 2007. SCCP/1098/07. https://ec.europa.eu/health/ph_risk/committees/04_sccp/docs/sccp_o_105.pdf.

Scientific Committee on Consumer Safety (SCCS). "Opinion on Hydroxyethyl-pphenylenediamine sulfate, Colipa n° A80". Mar. 23, 2006. SCCS/1310/10. https://ec.europa.eu/health/scientific_committees/consumer_safety/docs/sccs_o_017.pdf.

\* cited by examiner

OXIDATIVE DYEING AGENT FOR KERATIN FIBERS COMPRISING NOVEL DYE PRECURSOR COMBINATIONS

FIELD OF INVENTION

The subject of the present application is an agent for the oxidative dyeing of keratinous fibers, in particular human hair, which contains the coupling oxidation dye precursors 2-(1,3-benzodioxol-5-ylamino)ethanol and 1-phenyl-3-methylpyrazol-5-one in combination with at least one oxidation base.

BACKGROUND

Changing the color of keratin fibers, especially hair, is an important area of modern cosmetics. As a result, the appearance of the hair can be adapted both to current fashion trends and to the individual wishes of the individual. The expert knows different possibilities for changing the hair color. The hair color can be changed temporarily by using substantive dyes, which are also called direct dyes. The substantive or direct dyes bind to the hair mainly at its surface, but to a certain degree also diffuse into the hair fiber. The dyeing with substantive or direct dyes is associated with little damage to the hair, but a disadvantage is the relatively low fastness and the quick washability of the coloration obtained with direct dyes.

If consumers desire a long-lasting color result or a shade lighter than their original hair color, oxidative color modifiers are commonly used. So-called oxidation dyes are used for permanent, intensive dyeings with appropriate fastness properties. Such colorants usually contain oxidation dye precursors, so-called developer components (oxidation bases) and coupler components, which form the actual dyes in situ after having been combined with hydrogen peroxide in an aqueous medium. Oxidation dyes are characterized by long-lasting dyeing results.

Oxidative colorants have been used for decades. They are determined for the extracorporal use on keratin fibers like head hair, eyelashes and eye brows only, but during application, contact of the dyeing agent with the scalp cannot completely be avoided. In order to guarantee the highest possible product safety for the customers, the commercially used oxidation dye precursors are continuously monitored for their physiological compatibility, for example by the Scientific Committee on Consumer Products (SCCP), an advisory board of the European Commission. It is well-known that some of the oxidation dye precursors, especially some of the para-phenylene diamine-type oxidation bases, may have some sensitizing potential. Therefore, customers are advised to do a pre-check with a small amount of the dyeing agent on the skin before using the dyeing agent on the hair to rule out any allergic reaction during or after the dyeing process. Apart from skin sensitizing, other physiological effects are monitored as well.

Resorcinol, 4-chlororesorcinol and 2-methyl resorcinol are common oxidation dye precursors of the coupler type. In their latest opinion of March 2021, the SCCP concluded that the use of resorcinol in oxidative hair dye agents is considered safe in a resorcinol concentration of up to 1.25 weight-% in the ready-to-use mixture. The SCCP mentioned that resorcinol exerts anti-thyroid effects. However, while a clear level of exposure needed for such an effect cannot be derived from the available studies in humans, most of these studies point to a relatively much higher level of exposure than is the case from cosmetics.

SUMMARY OF THE INVENTION

In order to take into account some consumers' concerns on product safety, the underlying objective of this invention was to provide an agent for the oxidative dyeing of keratinous fibers, in particular human hair, which allows to cover a broad colour spectrum, especially a natural line of shades including cool natural and warm naturals and gold shade series, which results in colorations with high fastness properties, all without compromising product safety.

Surprisingly, it was found that with the combination of (A) the coupling oxidation dye precursor 2-(1,3-benzodioxol-5-ylamino)ethanol and (B) the coupling oxidation dye precursor 1-phenyl-3-methylpyrazol-5-one and furthermore (C) at least one oxidation base, agents for the oxidative dyeing of keratinous fibers are obtained which provide a natural line of shades including cool natural and warm naturals and gold shade series without using couplers of the resorcinol type.

The INCI name for 2-(1,3-benzodioxol-5-ylamino)ethanol is hydroxyethyl-3,4-methylenedioxyaniline. Another synonym for 2-(1,3-benzodioxol-5-ylamino)ethanol is 1-beta-hydroxyethyl-3,4-methylenedioxyaniline. Agents for the oxidative dyeing of keratinous fibers, in particular human hair, containing the coupling oxidation dye precursor 2-(1,3-benzodioxol-5-ylamino)ethanol and/or one of its physiologically tolerated salts are known in the prior art from U.S. Pat. No. 4,395,262A and DE3028202A1, furthermore also from GB2239265A1 and EP400330A1.

DETAILED DESCRIPTION OF THE INVENTION

The subject of the present invention is an agent for the oxidative dyeing of keratinous fibers, in particular human hair, which contains
  (A) the coupling oxidation dye precursor 2-(1,3-benzodioxol-5-ylamino)ethanol and/or at
    least one of its physiologically tolerated salts, and
  (B) the coupling oxidation dye precursor 1-phenyl-3-methylpyrazol-5-one and/or at least one
    of its physiologically tolerated salts, and
  (C) at least one oxidation dye precursor of the oxidation base-type,
wherein the agent is further free or substantially free of dissolved hydrogen peroxide.

A further subject of the present invention is a multicomponent kit-of-parts for oxidative dyeing of keratinous fibers, in particular human hair, comprising at least two separately packaged components (C1) and (C2), wherein
  the first component (C1), being free or substantially free of dissolved hydrogen peroxide, comprises
    (A) the coupling oxidation dye precursor 2-(1,3-benzodioxol-5-ylamino)ethanol and/or at least one of its physiologically tolerated salts, and
    (B) the coupling oxidation dye precursor 1-phenyl-3-methylpyrazol-5-one and/or at
      least one of its physiologically tolerated salts, and
    (C) at least one oxidation dye precursor of the oxidation base-type,
  the second component (C2) is an acidic aqueous hydrogen peroxide-containing composition.

A further subject of the present invention is a process for the oxidative hair dyeing of keratinous fibers, in particular human hair, in which an agent according to the invention is mixed with an acidic, aqueous hydrogen peroxide-containing composition and directly afterwards applied to the fibers, in particular the hair, is left there on the fibers for a time of from 1 to 60 minutes, preferably from 20 to 45 minutes, at room temperature and/or at least 30° C., the fibers, in particular the hair, are then rinsed with water and/or a cleansing composition and, if desired, an aftertreatment agent is applied to the fibers, in particular the hair, which is optionally rinsed out, and the hair is then dried.

Keratinic fibers, keratin containing fibers or keratin fibers are to be understood as furs, wool, feathers, and in particular human hair.

The terms "oxidative dyeing agents" and "agent for the oxidative dyeing of keratinous fibers, in particular human hair" as used in the invention refer to oxidative dyeing agents containing at least one oxidation dye precursors of the so-called developer-type, which are also called "oxidation bases", and at least one oxidation dye precursor of the so-called coupler-type oxidation dye precursors. The coloration is formed by the presence of an oxidizing agent (C) other than atmospheric oxygen, which is preferably hydrogen peroxide. Depending on the amount of oxidant used, the keratin fiber is simultaneously lightened to a greater or lesser extent during dyeing, since the oxidant not only initiates the dye formation process of developers and couplers, but also oxidatively destroys the hair's own pigments (melanins).

As used herein, the term "substantially free of dissolved hydrogen peroxide" refers to less than 0.01 wt %, or less than 0.001 wt %, or the complete absence, i.e. 0 wt %, of dissolved hydrogen peroxide, each based on the total weight of the agent or composition.

As used here, the term "substantially free of resorcinol" or "substantially free of any resorcinol compound" of a defined structure (e.g. structure (I) or structure (II) refers to less than 0.01 wt %, or less than 0.001 wt %, or about 0% based on the total weight of the agent or composition.

Preferred physiologically acceptable salts of the oxidation dye precursors that comprise one or more amino groups are the hydrochlorides (monohydrochloride×HCl, or dihydrochloride×2 HCl), the sulfates (×H$_2$SO$_4$) and the hydrobromides (monohydrobromide×HBr, or dihydrobromide×2 HBr) of the respective precursor compound. Further acids that can form physiologically acceptable salts of the oxidation dye precursors can be selected from lactic acid, citric acid, taurine, succinic acid, malic acid, oxalic acid, malonic acid, glutaric acid, adipic acid, pimelic acid, suberic acid, azelaic acid, sebacic acid, tartaric acid, alpha-ketoglutaric acid and beta-ketoglutaric acid as well as mixtures of these acids.

Preferred agents according to the present invention are characterized in that they comprise the coupling oxidation dye precursor 2-(1,3-benzodioxol-5-ylamino)ethanol and/or at least one of its physiologically tolerated salts in a total amount of 0.01 to 5.0% by weight, preferably 0.03 to 3.0% by weight, particularly preferably 0.05 to 1.5% by weight, the amounts being based on the weight of the agent.

Further preferred agents according to the present invention are characterized in that they comprise the coupling oxidation dye precursor 1-phenyl-3-methylpyrazol-5-one and/or at least one of its physiologically tolerated salts in a total amount of 0.01 to 1.0% by weight, preferably 0.05 to 0.5% by weight, particularly preferably 0.08 to 0.2% by weight, the amounts being based on the weight of the agent.

Further preferred agents according to the present invention are characterized in that the at least one oxidation base (C) is selected from para-phenylenediamine, toluene-2,5-diamine, 2-methoxymethyl-para-phenylenediamine, 2-(2,5-diaminophenyl)ethanol, N,N-bis-(2-hydroxyethyl)-p-phenylenediamine, 4-amino-3-methylphenol, 4-aminophenol, 4,5-diamino-1-(2-hydroxyethyl)-1H-pyrazole, 2-(1,2-dihydroxyethyl)-p-phenylenediamine, N,N'-bis-(2-hydroxyethyl)-N,N'-bis-(4-aminophenyl)-1,3-diaminopropane-2-ol, bis-(2-hydroxy-5-aminophenyl)methane, 1,3-bis-(2,5-diaminophenoxy)-propane-2-ol, N,N'-bis-(4-aminophenyl)-1,4-diazacycloheptane, 1,10-bis-(2,5-diaminophenyl)-1,4,7,10-tetraoxadecane, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo-[1,2-a]-pyrazole-1-one and their physiologically tolerated salts as well as mixtures of the aforementioned substances.

Further extraordinarily preferred agents according to the present invention are characterized in that the at least one oxidation base (C) is selected from para-phenylenediamine, toluene-2,5-diamine, 2-methoxymethyl-para-phenylenediamine, 2-(2,5-diaminophenyl)ethanol, N,N-bis-(2-hydroxyethyl)-p-phenylenediamine, 4-amino-3-methylphenol, 4-aminophenol, 4,5-diamino-1-(2-hydroxyethyl)-1H-pyrazole, and their physiologically tolerated salts as well as mixtures of the aforementioned substances.

Further preferred agents according to the present invention are characterized in that the at least one oxidation base and/or at least one of its physiologically tolerated salts is contained in a total amount of 0.001 to 5.0% by weight, preferably 0.01 to 3.0% by weight, particularly preferably 0.05 to 1.5% by weight, the amounts being based on the weight of the agent.

Further preferred agents according to the present invention are characterized in that they comprise—beyond 2-(1,3-benzodioxol-5-ylamino)ethanol and 1-phenyl-3-methylpyrazol-5-one—at least one additional coupling oxidation dye precursor and/or at least one of its physiologically tolerated salts in a total amount of 0.001 to 5.0% by weight, preferably 0.01 to 3.0% by weight, particularly preferably 0.05 to 1.5% by weight, the amounts being based on the weight of the agent.

Further preferred agents according to the present invention are characterized in that the at least one additional coupling oxidation dye precursor is selected from meta-aminophenols, meta-phenylenediamines, naphthols, pyridines, ortho-aminophenols, indoles and indolines, their physiologically tolerated salts as well as mixtures of these substances.

In some cases, especially for some shades, resorcinol-type couplers, especially resorcinol, (1,3-dihydroxybenzene), 2-methylresorcinol and 4-chlororesorcinol, can serve as a further additional coupling oxidation dye precursors.

Especially preferred additional coupling oxidation dye precursors of the meta-aminophenol type are selected from 3-aminophenol (meta-aminophenol), 5-amino-2-methylphenol (4-amino-2-hydroxytoluene), 3-amino-2-chloro-6-methylphenol, 2-hydroxy-4-aminophenoxyethanol, 5-amino-4-chloro-2-methylphenol, 5-(2-hydroxyethyl)-amino-2-methylphenol and 2,4-dichloro-3-aminophenol and their physiologically tolerated salts as well as mixtures of these substances.

Especially preferred additional coupling oxidation dye precursors of the m-phenylenediamine type are selected from 1,3-phenylenediamine, 2-(2,4-diaminophenoxy)ethanol, 1-methoxy-2-amino-4-(2-hydroxyethylamino)benzene, 1,3-bis(2,4-diaminophenoxy)propane, 1,3-bis(2,4-diaminophenyl)propane, 2,6-bis-(2'-hydroxyethylamino)-1-methylbenzene, 2-({3-[(2-hydroxyethyl)amino]-4-methoxy-5- methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 3-amino-4-(2-methoxyethoxy)-5-methylphenylamine and 1-amino-3-bis-(2-hydroxyethyl)aminobenzene and their physiologically tolerated salts as well as mixtures of these substances.

Especially preferred additional coupling oxidation dye precursors of the naphthol type are selected from 1-naphthol, 1,5-dihydroxynaphthalene, 2,7-dihydroxynaphthalene, 1,7-dihydroxynaphthalene and 1,8-dihydroxynaphthalene as well as mixtures of these substances.

Especially preferred additional coupling oxidation dye precursors of the pyridine type are selected from 2-amino-3-hydroxypyridine, 3-amino-2-methylamino-6-methoxypyridine, 2,6-dihydroxy-3,4-dimethylpyridine and 3,5-diamino-2,6-dimethoxypyridine and their physiologically tolerated salts as well as mixtures of these substances.

An especially preferred additional coupling oxidation dye precursor of the ortho-aminophenol type is selected from 2-aminophenol and its physiologically tolerated salts.

Especially preferred additional coupling oxidation dye precursors of the indole type or indoline type are selected from 4-hydroxyindole, 6-hydroxyindole, 7-hydroxyindole, 4-hydroxyindoline, 6-hydroxyindoline and 7-hydroxyindoline and their physiologically tolerated salts as well as mixtures of these substances.

Further especially preferred agents according to the present invention are characterized in that they comprise at least one additional coupling oxidation dye precursor, selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 1,3-phenylenediamine, 2-(2,4-diaminophenoxy)ethanol, 1-methoxy-2-amino-4-(2-hydroxyethylamino)benzene, 1,3-bis(2,4-diaminophenoxy)propane, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 3-amino-4-(2-methoxyethoxy)-5-methylphenylamine, 1-amino-3-bis-(2-hydroxyethyl)aminobenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-naphthol, 1,5-dihydroxynaphthalene, 2,7-dihydroxynaphthalene, 1,7-dihydroxynaphthalene, 1,8-dihydroxynaphthalene, 2-methylresorcinol, 4-chlororesorcinol, 4-hydroxyindole, 6-hydroxyindole, 7-hydroxyindole, 4-hydroxyindoline, 6-hydroxyindoline and/or 7-hydroxyindoline and their physiologically tolerated salts as well as mixtures of the aforementioned substances.

Further extraordinarily preferred agents according to the present invention are characterized in that they comprise at least one additional coupling oxidation dye precursor, selected from 3-aminophenol, 5-amino-2-methylphenol, 2-amino-3-hydroxypyridine, 2-(2,4-diaminophenoxy)ethanol, 1-naphthol, 1-methoxy-2-amino-4-(2-hydroxy-ethylamino)benzene, 1,3-bis(2,4-diaminophenoxy)propane, 3-amino-2-methylamino-6-methoxypyridine, 2,7-dihydroxynaphthalene and their physiologically tolerated salts as well as mixtures of the aforementioned substances, more preferably selected from 3-aminophenol, 5-amino-2-methylphenol, 2-amino-3-hydroxypyridine, 2-(2,4-diaminophenoxy)ethanol and 1-naphthol, their physiologically tolerated salts as well as mixtures of the aforementioned substances.

Further extraordinarily preferred agents according to the present invention are characterized in that they are free or substantially free of resorcinol (1,3-dihydroxybenzene).

Further extraordinarily preferred agents according to the present invention are characterized in that they are free or substantially free of any resorcinol compound of structure (I)

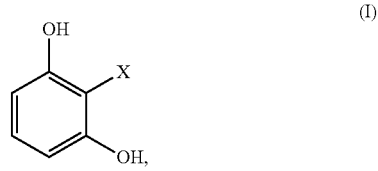

in which
X means a hydrogen atom or a C1-C10 alkyl group, preferably a hydrogen atom or a methyl group.

Further extraordinarily preferred agents according to the present invention are characterized in that they are free or substantially free of any resorcinol compound of structure (II)

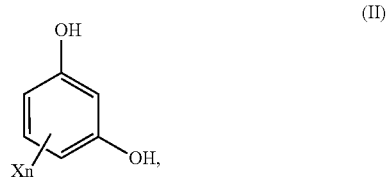

in which
X means a chlorine atom or a C1-C10 alkyl group and n means an integer from zero to 4.

Further extraordinarily preferred agents according to the present invention are characterized in that they comprise a dye precursor mixture, which consists essentially of one of the following combinations, using the free bases or their physiologically tolerated salts:

2-(1,3-benzodioxol-5-ylamino)ethanol, 1-phenyl-3-methylpyrazol-5-one, 3-aminophenol and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diamino-phenyl)ethanol and mixtures of the aforementioned oxidation bases;

2-(1,3-benzodioxol-5-ylamino)ethanol, 1-phenyl-3-methylpyrazol-5-one, 3-aminophenol, 5-amino-2-methylphenol and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diaminophenyl)ethanol and mixtures of the aforementioned oxidation bases;

2-(1,3-benzodioxol-5-ylamino)ethanol, 1-phenyl-3-methylpyrazol-5-one, 3-aminophenol, 5-amino-2-methylphenol, 2,4-diaminophenoxyethanol and at least one of the oxidation bases para-phenylenediamine, N,N-bis-(2-hydroxyethyl)-p-phenylenediamine, 4-amino-3- methylphenol, 4-aminophenol, toluene-2,5-diamine, 2-methoxymethyl-para-phenylenediamine, 2-(2,5-diaminophenyl)ethanol and mixtures of the aforementioned oxidation bases;

2-(1,3-benzodioxol-5-ylamino)ethanol, 1-phenyl-3-methylpyrazol-5-one, 3-aminophenol, 2,4-diaminophenoxyethanol and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diaminophenyl)ethanol and mixtures of the aforementioned oxidation bases;

2-(1,3-benzodioxol-5-ylamino)ethanol, 1-phenyl-3-methylpyrazol-5-one, 3-aminophenol, 2,4-diaminophenoxyethanol, 2-amino-3-hydroxypyridine, and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diaminophenyl)ethanol and mixtures of the aforementioned oxidation bases;

2-(1,3-benzodioxol-5-ylamino)ethanol, 1-phenyl-3-methylpyrazol-5-one, 3-aminophenol, 2-amino-3-hydroxypyridine, and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diaminophenyl)ethanol and mixtures of the aforementioned oxidation bases;

2-(1,3-benzodioxol-5-ylamino)ethanol, 1-phenyl-3-methylpyrazol-5-one, 3-aminophenol, 2-amino-3-hydroxypyridine, 1-naphthol, and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diaminophenyl)ethanol and mixtures of the aforementioned oxidation bases;

2-(1,3-benzodioxol-5-ylamino)ethanol, 1-phenyl-3-methylpyrazol-5-one, 3-aminophenol, para-phenylenediamine, N,N-bis-(2-hydroxyethyl)-p-phenylenediamine, 4-amino-3-methylphenol and 4-aminophenol;

2-(1,3-benzodioxol-5-ylamino)ethanol, 1-phenyl-3-methylpyrazol-5-one, 3-aminophenol, 5-amino-2-methylphenol, para-phenylenediamine, N,N-bis-(2-hydroxy-ethyl)-p-phenylenediamine, 4-amino-3-methylphenol and 4-aminophenol;

2-(1,3-benzodioxol-5-ylamino)ethanol, 1-phenyl-3-methylpyrazol-5-one, 3-aminophenol, 5-amino-2-methylphenol, 2,4-diaminophenoxyethanol, para-phenylenediamine, N,N-bis-(2-hydroxyethyl)-p-phenylenediamine, 4-amino-3-methylphenol and 4-aminophenol;

2-(1,3-benzodioxol-5-ylamino)ethanol, 1-phenyl-3-methylpyrazol-5-one, 3-aminophenol, 2,4-diaminophenoxyethanol, para-phenylenediamine, N,N-bis-(2-hydroxyethyl)-p-phenylenediamine, 4-amino-3-methylphenol and 4-aminophenol;

2-(1,3-benzodioxol-5-ylamino)ethanol, 1-phenyl-3-methylpyrazol-5-one, 3-aminophenol, 2,4-diaminophenoxyethanol, 2-amino-3-hydroxypyridine, para-phenylenediamine, N,N-bis-(2-hydroxyethyl)-p-phenylenediamine, 4-amino-3-methylphenol and 4-aminophenol;

2-(1,3-benzodioxol-5-ylamino)ethanol, 1-phenyl-3-methylpyrazol-5-one, 3-aminophenol, 2-amino-3-hydroxypyridine, para-phenylenediamine, N,N-bis-(2-hydroxyethyl)-p-phenylenediamine, 4-amino-3-methylphenol and 4-aminophenol;

2-(1,3-benzodioxol-5-ylamino)ethanol, 1-phenyl-3-methylpyrazol-5-one, 3-aminophenol, 2-amino-3-hydroxypyridine, 1-naphthol, para-phenylenediamine, N,N-bis-(2-hydroxyethyl)-p-phenylenediamine, 4-amino-3-methylphenol and 4-aminophenol.

Further preferred agents according to the present invention as contemplated herein can also contain at least one direct dye selected from the group including anionic, non-ionic and cationic dyes. With the help of these direct dyes a broader range of colorations can be realized, ranging from very natural shades to very fashioned shades.

Particularly preferred are one or more nonionic direct dyes from the group consisting of 2-[(2-nitrophenyl)amino]ethanol (HC Yellow 2), 2-(3-nitro-6-(2'-hydroxyethylamino)-phenoxy)ethanol (HC Yellow 4), N'-2-hydroxyethyl-4-nitro-ortho-phenylenediamine (HC Yellow 5), 2-nitro-4'-hydroxydiphenylamine (HC Orange 1), 4-amino-2-nitrodiphenylamine (HC Red 1), 4-(2-hydroxyethyl)amino-3-nitroaniline (HC Red 3), 1-amino-2-nitro-4-(beta-hydroxyethyl)-aminobenzene (HC Red 7), 1-amino-2-nitro-4-bis(beta-hydroxyethyl)-aminobenzene (HC Red 13), 1-Hydroxy-3-nitro-4-(3-hydroxypropylamino)benzene (HC Red BN), 1-beta-hydroxyethylamino-2-nitro-4-bis-(beta-hydroxyethyl)aminobenzene (HC Blue 2), 4-[di(2-hydroxyethyl)amino]-1-[(2-methoxyethyl)amino]-2-nitrobenzene (HC Blue 11), 1-(beta-hydroxyethyl)amino-2-nitro-4-N-ethyl-N-(beta-hydroxyethyl)aminobenzene (HC Blue 12), 1-amino-3-methyl-4(2-hydroxyethyl)-amino-6-nitrobenzene (HC Violet 1), 1,4-diaminoanthraquinone (Disperse Violet 1), 1,4-amino-4-(methylamino)anthraquinone (Disperse Violet 4), 2,2'-[4-(4-aminophenylazo)phenylimino]diethanol (Disperse Black 9), 1,4-diamino-2-nitrobenzene, 2-amino-4-nitrophenol, 1,4-bis(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 4-amino-3-nitrophenol, 2-[(4-amino-2-nitrophenyl)amino]benzoic acid and its salts, 4-[(3-hydroxypropyl)amino]-3-nitrophenol, 4-nitro-ortho-phenylenediamine, 6-nitro-1,2,3,4-tetrahydroquinoxaline, 2-hydroxy-1,4-naphthoquinone, picramic acid and its salts, and 4-ethylamino-3-nitrobenzoic acid and its salts.

Particularly preferred are one or more anionic direct dyes from the group consisting of Acid Yellow 1, Acid Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Bromophenol Blue and Tetrabromophenol Blue.

Particularly preferred are one or more cationic direct dyes from the group consisting of cationic triphenylmethane dyes, such as Basic Blue 7, Basic Blue 26, Basic Violet 2 and Basic Violet 14, aromatic systems substituted with a quaternary nitrogen group, such as Basic Yellow 57, Basic Red 76, Basic Blue 99, Basic Brown 16 and Basic Brown 17, cationic anthraquinone dyes such as HC Blue 16 (Bluequat B), direct dyes containing a heterocycle containing at least one quaternary nitrogen atom, in particular Basic Yellow 87, Basic Orange 31 and Basic Red 51, and cationic direct dyes marketed under the trademark Arianor.

Further preferred agents according to the present invention are characterized in that they comprise at least one direct dye and/or at least one of its physiologically tolerated salts, in a total amount of 0.001 to 3.0% by weight, preferably 0.01 to 2.0% by weight, particularly preferably 0.1 to 1.0% by weight, the amounts being based on the weight of the agent.

Further preferred dyeing agents according to the present invention are characterized in that they comprise at least one direct dye and/or at least one of its physiologically tolerated salts, which is selected from the group consisting of 2-[(2-nitro-phenyl)amino] ethanol (HC Yellow 2), 2-(3-nitro-6-(2'-hydroxyethylamino)-phenoxy)ethanol (HC Yellow 4), N'-2-hydroxyethyl-4-nitro-ortho-phenylenediamine (HC Yellow 5), 2-nitro-4'-hydroxydiphenylamine (HC Orange 1), 4-amino-2-nitrodiphenylamine (HC Red 1), 4-(2-hydroxyethyl)amino-3-nitroaniline (HC Red 3), 1-amino-2-nitro-4-(beta-hydroxyethyl)-aminobenzene (HC Red 7), 1-amino-2-nitro-4-bis(beta-hydroxyethyl)-aminobenzene (HC Red 13), 1-hydroxy-3-nitro-4-(3-hydroxypropylamino) benzene (HC Red BN), 1-beta-hydroxyethylamino-2-nitro-4-bis-(beta-hydroxyethyl)aminobenzene (HC Blue 2), 4-[di(2-hydroxyethyl)amino]-1-[(2-methoxyethyl)amino]-2-nitrobenzene (HC Blue 11), 1-(beta-hydroxyethyl)amino-2-nitro-4-N-ethyl-N-(beta-hydroxyethyl)aminobenzene (HC Blue 12), 1-amino-3-methyl-4(2-hydroxyethyl)-amino-6-nitrobenzene (HC Violet 1), 1,4-diaminoanthraquinone (Disperse Violet 1), 1,4-amino-4-(methylamino)anthraquinone (Disperse Violet 4), 2,2'-[4-(4-aminophenylazo)phenylimino]diethanol (Disperse Black 9), 1,4-diamino-2-nitrobenzene, 2-amino-4-nitrophenol, 1,4-bis(2-hydroxyethyl) amino-2-nitrobenzene, 3-nitro-4-(2-hydroxyethyl) aminophenol, 2-(2-hydroxyethyl)amino-4,6-dinitrophenol, 4-[(2-hydroxyethyl)amino]-3-nitro-1-methylbenzene, 4-amino-3-nitrophenol, 2-[(4-amino-2-nitrophenyl)amino] benzoic acid and its salts, 4-[(3-hydroxypropyl)amino]-3-nitrophenol, 4-nitro-ortho-phenylenediamine, 6-nitro-1,2,3, 4-tetrahydroquinoxaline, 2-hydroxy-1,4-naphthoquinone, picramic acid and its salts, and 4-ethylamino-3-nitrobenzoic acid and its salts, Acid Yellow 1, Acid Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Bromophenol Blue, Tetrabromophenol Blue, Basic Blue 7, Basic Blue 26, Basic Violet 2, Basic Violet 14, Basic Yellow 57, Basic Red 76, Basic Blue 99, Basic Brown 16, Basic Brown 17, HC Blue 16 (Bluequat B), Basic Yellow 87, Basic Orange 31 and Basic Red 51, as well as mixtures of the aforementioned substances.

The agents for oxidative dyeing according to the invention contain (A) the coupling oxidation dye precursor 2-(1, 3-benzodioxol-5-ylamino)ethanol and/or at least one of its physiologically tolerated salts, (B) the coupling oxidation dye precursor 1-phenyl-3-methylpyrazol-5-one and/or at least one of its physiologically tolerated salts, and (C) at least one oxidation dye precursor of the oxidation base-type preferably in a cosmetic carrier, particularly preferred in a suitable aqueous, alcoholic, or aqueous-alcoholic carrier, which is free or substantially free of dissolved hydrogen peroxide. For oxidative coloring, such carriers may be, for example, creams, emulsions, gels or foaming or foamable solutions, such as shampoos, foam aerosols, foam formulations or other preparations suitable for application to the hair. Particularly preferred agents for oxidative dyeing of keratinous fibers are creams or emulsions, especially oil-in-water emulsions, as well as aqueous gels.

In order to achieve the desired long-lasting coloring or lightening of the keratin fibers, the ready-to-use mixture of the dyeing agent to be applied on the fibers should exhibit a pH in the range from 6.5 to 11.5, preferably 8.0 to 11.0, more preferably 8.5 to 10.5, particularly preferably 9.0 to 10.0, in each case measured at 20° C. At these pH values, the outer keratin fiber layer opens optimally to absorb the oxidation dye precursors, and the desired effect of the peroxide compound is optimally achieved. The aqueous hydrogen peroxide-containing composition (C2) has to have an acidic pH in the range from 2.0 to 6.5, preferably 2.5 to 5.5, particularly preferably 2.8 to 5.0, in each case measured at 20° C., in order to be shelf-stable until the moment of use for being mixed with the dyeing agent according to the invention. Therefore, the dyeing agent according to the invention, being component (C1) of the dyeing kit, should exhibit a pH in the range from 6.5 to 12.0, preferably 8.0 to 11.0, more preferably 8.5 to 10.5, particularly preferably 9.5 to 10.1, in each case measured at 20° C. Therefore, preferred dyeing agents according to the invention comprise at least one alkalizing agent.

The alkalizing agents usable in the dyeing agent according to the invention are preferably selected from the group formed by ammonia, alkanolamines, basic amino acids, as well as inorganic alkalizing agents such as (earth) alkali metal hydroxides, (earth) alkali metal metasilicates, (earth) alkali metal phosphates and (earth) alkali metal hydrogen phosphates. Preferred inorganic alkalizing agents are sodium hydroxide, potassium hydroxide, sodium silicate and sodium metasilicate. The alkanolamines which can be used as alkalizing agents are preferably selected from primary amines with a $C_2$-$C_6$ alkyl base body which carries at least one hydroxyl group. Particularly preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, and 2-amino-2-methylpropane-1,3-diol. Alkanolamines which are particularly preferred according to the invention are selected from the group consisting of 2-aminoethan-1-ol, 2-amino-2-methylpropan-1-ol and 2-amino-2-methylpropane-1,3-diol. The basic amino acids which can be used as alkalizing agents according to the invention are preferably selected from the group formed by arginine, lysine, ornithine, and histidine, particularly preferably arginine. Further preferred dyeing agents according to the present invention are characterized in that they comprise at least one alkalizing agent selected from the group formed by ammonia, alkanolamines and basic amino acids, in particular at least one alkalizing agent selected from the group formed by ammonia, monoethanolamine and arginine as well as mixtures of these substances.

The cosmetic carrier for dyeing agent according to the invention may be formulated as a water-based emulsion, an aqueous solution, which is sprayable, an aqueous cream, an aqueous gel, an aqueous shampoo or an anhydrous powder or anhydrous paste. Particularly preferred agents for oxidative dyeing of keratinous fibers are creams or emulsions, especially oil-in-water emulsions, as well as aqueous gels.

Further preferred dyeing agents according to the invention contain at least one linear saturated alkanol having 12-30 carbon atoms. Those linear saturated alkanol having 12-30 carbon atoms serve as structuring agents, especially for emulsions and creams. Besides, they can help to form a lamellar gel network, which can suppress the volatilization of ammonia from the alkalizing agent aqueous ammonia. For the purposes of the present disclosure, alkanols with at least 8 carbon atoms are considered fatty substances, not surfactants.

Preferred linear saturated alkanols having 12 to 30 carbon atoms, especially 16 to 22 carbon atoms, are selected from cetyl alcohol, stearyl alcohol, arachidyl alcohol, behenyl alcohol and lanolin alcohol, and mixtures of these alkanols. Alkanol mixtures particularly preferred as contemplated herein are those obtainable in the technical hydrogenation of vegetable and animal fatty acids. Preferably, the total amount of at least one linear saturated alkanol having 12 to 30 carbon atoms in the dyeing agent according to the invention is from about 0.1 to about 20% by weight, preferably from about 0.5 to about 16% by weight and particularly preferably from about 3 to about 10% by weight, in each case based on the weight of the dyeing agent according to the invention.

Further preferred dyeing agents according to the invention contain at least one surfactant or emulsifier.

For the purposes of the present application, surfactants and emulsifiers are amphiphilic (bifunctional) compounds which include at least one hydrophobic and at least one hydrophilic part of the molecule. The hydrophobic radical is preferably a hydrocarbon chain with 8 to 28 carbon atoms, which can be saturated or unsaturated, linear, or branched. This $C_8$-$C_{28}$ alkyl chain is particularly preferably linear. Basic properties of surfactants and emulsifiers are the oriented absorption at interfaces as well as the aggregation to micelles and the formation of lyotropic phases.

When selecting surfactants suitable as contemplated herein, it may be preferable to use a mixture of surfactants to optimally adjust the stability of the oxidative dye precursors as contemplated herein.

Preferably, the total amount of at least one surfactant in the dyeing agent according to the invention is about 0.1 to about 20% by weight, preferably from about 0.5 to about 10% by weight and particularly preferably from about 1.5 to about 5% by weight, in each case based on the weight of the dyeing agent according to the invention.

Preferred surfactants and emulsifiers are selected from anionic, cationic, zwitterionic, amphoteric and nonionic surfactants and emulsifiers and mixtures thereof. These substances are described below.

Preferred dyeing agent according to the invention are characterized in that the at least one surfactant present is selected from nonionic surfactants and anionic surfactants and mixtures thereof.

Suitable anionic surfactants are all anionic surface-active substances suitable for use on the human body which have a water-solubilizing anionic group, for example a carboxylate, sulfate, sulfonate or phosphate group, and a lipophilic alkyl group with about 8 to 30 C atoms (carbon atoms), preferably 8 to 24 C atoms, in the molecule. In addition, glycol or polyglycolether groups, ester, ether and amide and hydroxyl groups may also be present in the molecule. Examples of suitable anionic surfactants are, in each case in the form of the sodium, potassium and ammonium as well as the mono-, di- and trialkanol-ammonium salts with 2 to 4 C atoms in the alkanol group, linear and branched fatty acids with 8 to 30 C atoms (soaps), polyethoxylated ether carboxylic acids, acyl sarcosides, acyl taurides, acyl isethionates, sulfosuccinic acid mono- and dialkyl esters and sulfosuccinic acid monoalkyl polyoxyethylene esters containing 1 to 6 ethylene oxide groups, linear alkane sulfonates, linear alpha-olefin sulfonates, sulfonates of unsaturated fatty acids with up to 6 double bonds, alpha-sulfofatty acid methyl esters of fatty acids, $C_8$-$C_{20}$ alkyl sulfates and $C_8$-$C_{20}$ alkyl ether sulfates with up to about 15 oxyethylene groups, mixtures of surface-active hydroxysulfonates, sulfated hydroxyalkyl polyethylene and/or hydroxyalkylene propylene glycol ethers, esters of tartaric acid or citric acid with ethoxylated or propoxylated fatty alcohols, optionally polyethoxylated alkyl and/or alkenyl ether phosphates, sulfated fatty acid alkylene glycol esters, and monoglyceride sulfates and monoglyceride ether sulfates. Preferred anionic surfactants are soaps, $C_8$-$C_{20}$ alkyl sulfates, $C_8$-$C_{20}$ alkyl ether sulfates and $C_8$-$C_{20}$ ether carboxylic acids with 8 to 20 C atoms in the alkyl group and up to about 12 ethylene oxide groups in the molecule. Sodium cetearyl sulfate is particularly preferred.

Preferably, the total amount of at least one anionic surfactant in the dyeing agent according to the invention is about 0.01 to about 10% by weight, preferably from about 0.1 to about 5% by weight and particularly preferably from about 1 to about 3% by weight, in each case based on the weight of the dyeing agent according to the invention.

Suitable cationic surfactants are all cationic surface-active substances suitable for use on the human body which have a water-solubilizing cationic group. Preferred cationic surfactants are selected from quaternary ammonium compounds and esterquats. Exemplary quaternary ammonium compounds are ammonium halides, in particular chlorides or bromides, such as alkyltrimethylammonium chlorides, dialkyldimethylammonium chlorides and trialkylmethylammonium chlorides, for example cetyltrimethylammonium chloride, stearyltrimethylammonium chloride, distearyldimethylammonium chloride, lauryldimethylammoniun chloride, lauryldimethylbenzylammonium chloride and tricetylmethylammonium chloride, and those imidazolium compounds known under the INCI names Quaternium-27, Quaternium-83 and Quaternium-87. The alkyl chains of the aforementioned surfactants have from about 10 to about 18 carbon atoms. Esterquats are substances which contain both at least one ester function and at least one quaternary ammonium group as a structural element. Exemplary esterquats are quaternized ester salts of fatty acids with triethanolamine, quaternized ester salts of fatty acids with diethanol-alkylamines and quaternized ester salts of fatty acids with 1,2-dihydroxypropyldialkylamines. Specific examples are methyl-N-(2-hydroxyethyl)-N,N-di(stearoyloxyethyl) ammonium compounds, bis-(palmitoyloxyethyl) hydroxyethylmethylammonium compounds, methyl-N,N-bis(stearoyloxyethyl)-N-(2-hydroxyethyl) ammonium compounds, methyl-N,N-bis(cocoyloxyethyl)-N-(2-hydroxyethyl) ammonium compounds or N,N-dimethyl-N, N-di(stearoyloxyethyl) ammonium compounds.

Preferably, the total amount of at least one cationic surfactant in the dyeing agent according to the invention is about 0.01 to about 10% by weight, preferably from about 0.1 to about 5% by weight and particularly preferably from about 1 to about 3% by weight, in each case based on the weight of the dyeing agent according to the invention.

Non-ionic surfactants used with particular preference are selected from about 20-100 moles of ethylene oxide per mole of ethoxylated castor oil, ethoxylated $C_8$-$C_{24}$ alkanols with about 1-200 moles of ethylene oxide per mole, ethoxylated $C_8$-$C_{24}$ carboxylic acids with about 1-200 moles of ethylene oxide per mole, with about 4-80 moles of ethylene oxide per mole of ethoxylated sorbitan monoesters of linear saturated and unsaturated $C_{12}$-$C_{30}$ carboxylic acids, which can be hydroxylated, especially those of myristic acid, palmitic acid, stearic acid or of mixtures of these fatty acids, alkyl mono- and oligoglycosides with 8 to 22 carbon atoms in the alkyl radical and their ethoxylated analogues, amidoamines, like stearamidopropyl dimethylamine, palmitamidopropyl dimethylamine, lauramidopropyl dimethylamine or behenamidopropyl dimethylamine, and mixtures of the aforementioned substances. The latter type, the amidoamines, are considered as cationic surfactants in an acidic medium, because the amine group is quaternized by a proton. As the agent according to the invention preferably is alkaline, the amidoamines are considered as being non-ionic surfactants.

The ethoxylated $C_8$-$C_{24}$ alkanols have the formula $R^1O(CH_2CH_2O)_nH$, where $R^1$ is a linear or branched alkyl and/or alkenyl radical containing 8-24 carbon atoms and n, the average number of ethylene oxide units per molecule, for numbers from about 1 to 200, preferably about 2 to 150, particularly preferably about 4 to 100, exceptionally preferably about 10 to 50, further exceptionally preferred about 12 to 30 or about 20 moles of ethylene oxide to 1 mole of caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol, and their technical mixtures. Adducts of about 1 to 200 moles of ethylene oxide with technical fatty alcohols with 12 to 18 carbon atoms, such as coconut, palm, palm kernel or tallow fatty alcohol, are also suitable. Particularly preferred are laureth-2, laureth-4, laureth-10, laureth-12, laureth-15, laureth-20, laureth-30, myreth-2, myreth-4, myreth-10, myreth-12, myreth-15, myreth-20, myreth-30, ceteth-2, ceteth-4, ceteth-10, ceteth-12, ceteth-15, ceteth-20, ceteth-30, ceteth-50, ceteth-100, ceteth-150, steareth-2, steareth-4, steareth-10, steareth-12, steareth-15, steareth-20, steareth-30, steareth-50, steareth-100, steareth-150, oleth-2, oleth-4, oleth-10, oleth-12, oleth-15, oleth-20, oleth-30, ceteareth-2, ceteareth-4, ceteareth-10, ceteareth-15, ceteareth-12, ceteareth-15, ceteareth-20, ceteareth-30, ceteareth-50, ceteareth-100, ceteareth-150, coceth-2, coceth-4, coceth-10, coceth-12, coceth-15, coceth-20, coceth-30, coceth-50 and coceth-100.

The ethoxylated $C_8$-$C_{24}$ carboxylic acids have the formula $R^1O(CH_2CH_2O)_nH$, where $R^1O$ is a linear or branched saturated or unsaturated acyl radical containing 8 to 24 carbon atoms and n, the average number of ethylene oxide units per molecule, for numbers from about 1 to 200, preferably about 10 to 50 moles ethylene oxide to 1 mole caprylic acid, 2-ethylhexanoic acid, capric acid, lauric acid, isotridecanoic acid, myristic acid, cetylic acid, palmitoleic acid, stearic acid, isostearic acid, oleic acid, elaidic acid, petroselic acid, arachyic acid, gadoleic acid, behenic acid, erucic acid and brassidic acid and their technical mixtures. Adducts of about 1 to 200, preferably about 10 to 50 moles ethylene oxide to technical fatty acids with 12 to 18 carbon atoms, such as coconut, palm, palm kernel or tallow fatty acids, are also suitable. Especially preferred are PEG-50-monostearate, PEG-100-monostearate, PEG-50-monooleate, PEG-100-monooleate, PEG-50-monolaurate and PEG-100-monolaurate.

Preferred sorbitan monoesters of linear saturated and unsaturated $C_{12}$-$C_{30}$ carboxylic acids ethoxylated with about 4-80 moles of ethylene oxide per mole, which may be hydroxylated, are selected from polysorbate-20, polysorbate-40, polysorbate-60, and polysorbate-80.

Other preferred nonionic surfactants are selected from $C_8$-$C_{22}$ alkyl mono- and oligoglycosides. $C_8$-$C_{22}$ alkyl mono- and oligoglycosides represent well-known, commercially available surfactants and emulsifiers. They are produced by etherification of monosaccharides, especially glucose, or oligosaccharides, especially glucose with an average degree of oligomerization in the range from 1 to 2, preferably 1.2-1.4, with primary alcohols containing 8 to 22 carbon atoms. Particularly preferred $C_8$-$C_{22}$ alkyl mono- and oligoglycosides are selected from octyl glucoside, decyl glucoside, lauryl glucoside, palmityl glucoside, isostearyl glucoside, stearyl glucoside, arachidyl glucoside and behenyl glucoside, and mixtures thereof.

Other nonionic surfactants suitable as contemplated herein contain, for example, a polyol group, a polyalkylene glycol ether group or a combination of polyol and polyglycol ether group as the hydrophilic group. Such nonionic surfactants include
  polyglycerol esters and ethoxylated polyglycerol esters of C8-C30 fatty acids, such as poly(3)glycerol diisostearate and poly(2)glycerol polyhydroxystearate,
  ethoxylated mono-, di- and triesters of glycerol with C8-C30 fatty acids, such as glycerol monolaurate+20 ethylene oxide and glycerol monostearate+20 ethylene oxide, PEG-x Castor Oil with degree of ethoxylation x ranging from 1 to 80 or PEG-x Hydrogenated Castor Oil with degree of ethoxylation x ranging from 1 to 80,
  aminoxides of C8-C30 fatty amines,
  sugar fatty acid esters and adducts of ethylene oxide to sugar fatty acid esters, e.g., sucrose stearate, methyl glucose sesquistearate, PEG-20 methyl glucose sesquistearate or PEG-120 methyl glucose dioleate,
  adducts of ethylene oxide to fatty acid alkanolamides and fatty amines,
  fatty acid-N-alkylglucamides,
  monoesters of $C_8$-$C_{30}$ fatty acids and ethylene glycol, e.g. glycol monostearate or glycol distearate, and
  monoesters and diesters of $C_8$-$C_{30}$ fatty acids and glycerol, e.g. glycerol monostearate or glycerol distearate.

Preferred dyeing agents according to the invention are characterized in that they contain at least one nonionic surfactant selected from castor oil ethoxylated with about 20 to 100 moles of ethylene oxide per mole, ethoxylated $C_8$-$C_{24}$ alkanols with about 1 to 200 moles of ethylene oxide per mole, ethoxylated $C_8$-$C_{24}$ carboxylic acids with about 1 to 200 moles ethylene oxide per mole, with about 4 to 80 moles ethylene oxide per mole ethoxylated sorbitan monoesters of linear saturated and unsaturated $C_{12}$-$C_{30}$ carboxylic acids which may be hydroxylated, in particular those of myristic acid, palmitic acid, stearic acid or of mixtures of these fatty acids, alkyl mono- and oligoglycosides with 8 to 22 carbon atoms in the alkyl radical and their ethoxylated analogues, acyl glucamides derived from glucamine, polyglycerol esters and ethoxylated polyglycerol esters of C8-C30 fatty acids, ethoxylated mono-, di- and triesters of glycerol with C8-C30 fatty acids, amine oxides of C8-C30 fatty amines, sugar fatty acid esters and adducts of ethylene oxide with sugar fatty acid esters, adducts of ethylene oxide with fatty acid alkanolamides and fatty amines, fatty acid N-alkyl glucamides, monoesters of $C_8$-$C_{30}$ fatty acids and ethylene glycol, monoesters and diesters of $C_8$-$C_{30}$ fatty acids and glycerol, and mixtures of the aforementioned substances.

Preferably, the total amount of at least one nonionic surfactant in the dyeing agent according to the invention is about 0.01 to about 15% by weight, preferably from about 0.1 to about 10% by weight and particularly preferably from about 1 to about 6% by weight, in each case based on the weight of the dyeing agent according to the invention.

In another preferred embodiment, the total amount of at least one nonionic surfactant in the acidic aqueous hydrogen peroxide-containing composition (C2) of the multicomponent kit-of-parts for oxidative dyeing according to the invention is about 0.01 to about 15% by weight, preferably from about 0.1 to about 10% by weight and particularly preferably from about 1 to about 4% by weight, in each case based on the weight of the component (C2).

In another preferred embodiment, the dyeing agent according to the invention contains a total of about 0.1 to about 15% by weight, preferably from about 0.5 to about 10% by weight and particularly preferably from about 1 to about 7% by weight, in each case based on the weight of the dyeing agent according to the invention, of a mixture of nonionic and anionic surfactants.

Zwitterionic surfactants are surface-active compounds which bear at least one quaternary ammonium group and at least one carboxylate, sulphonate or sulphate group in the molecule. Particularly suitable zwitterionic surfactants are the so-called betaines such as the N-alkyl-N,N-dimethylammonium glycinates, for example cocoalkyl dimethylammonium glycinate, N-acyl-aminopropyl-N,N-dimethylammonium glycinate, for example cocoacylaminopropyl dimethylammonium glycinate, and 2-alkyl-3-carboxymethyl-3-hydroxyethyl imidazolines each having 8 to 18 carbon atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Amphoteric surfactants are surface-active compounds which, apart from a $C_8$-$C_{24}$ alkyl or acyl group, contain at least one free amino group and at least one —COOH or —$SO_3H$ group in the molecule and can form internal salts. Examples of suitable amphoteric surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having about 8 to 24 carbon atoms in the alkyl group. Particularly preferred amphoteric surfactants are N-cocoalkylaminopropionate, cocoacylaminoethylaminopropionate and $C_{12}$-$C_{18}$ acylsarcosine.

In a further preferred embodiment, the dyeing agent according to the invention contains a total of about 0.1 to about 10% by weight, preferably about 0.2 to about 6% by weight and particularly preferably from about 0.7 to about 2% by weight, in each case based on the weight of the dyeing agent according to the invention, of at least one zwitterionic or/and one amphoteric surfactant.

In a further preferred embodiment, the dyeing agent according to the invention contains cocamidopropyl betaine in an amount of about 0.1 to about 10% by weight, preferably about 0.2 to about 6% by weight and particularly preferably from about 0.7 to about 2% by weight, in each case based on the weight of the dyeing agent according to the invention.

Optionally, the dyeing agent according to the invention contains, based on its weight, at least one cosmetic oil in a total amount of about 0.01 to about 30% by weight, preferably from about 0.1 to about 15% by weight, particularly preferably from about 0.5 to about 5% by weight, exceptionally preferably from about 1 to about 2.5% by weight. In another preferred embodiment, the acidic aqueous hydrogen peroxide-containing composition (C2) of the multicomponent kit-of-parts for oxidative dyeing according to the invention contains a total of about 0.1 to about 30% by weight, preferably from about 0.4 to about 20% by weight and particularly preferably from about 1.0 to about 10% by weight, in each case based on the weight of component (C2), of at least one cosmetic oil. The cosmetic oil is liquid under normal conditions (20° C., 1013.25 mbar); essential oils and perfume oils or fragrances are not counted as cosmetic oils. Cosmetic oils which are liquid under normal conditions are not miscible with water. As contemplated herein, essential oils are mixtures of volatile components produced by steam distillation from vegetable raw materials, e.g., citrus oils. In so far as the present application refers to a cosmetic oil, it is always a cosmetic oil which is neither a perfume nor an essential oil, is liquid under normal conditions and is not miscible with water.

The definition of a fragrance within the meaning of the present notification is in line with the usual professional definition as it can be found in the ROMPP Chemie Lexikon, December 2007. According to this, a fragrance is a chemical compound with smell and/or taste that excites the receptors of the hair cells of the olfactory system (adequate stimulus). The physical and chemical properties required for this are a low molar mass of maximum 300 g/mol, a high vapor pressure, minimal water, and high lipid solubility as well as weak polarity and the presence of at least one osmophoric group in the molecule. To distinguish volatile, low-molecular substances which are normally, and also for the purposes of the present application, not considered and used as perfume but primarily as solvents, such as ethanol, propanol, isopropanol and acetone, from perfumes of the present disclosure, perfumes of the present disclosure have a molecular weight of 74 to 300 g/mol, contain at least one osmophoric group in the molecule and have an odor and/or taste, that is to say, they excite the receptors of the hair cells of the olfactory system.

Cosmetic oils which are particularly preferred as contemplated herein are selected from the esters of linear or branched saturated or unsaturated fatty alcohols having 2 to 30 carbon atoms with linear or branched saturated or unsaturated fatty acids having 2 to 30 carbon atoms, which may be hydroxylated. These include cetyl-2-ethylhexanoate, 2-hexyldecyl stearate, 2-hexyldecyl laurate, isodecyl neopentanoate, isononyl isononanoate, 2-ethylhexyl palmitate and 2-ethylhexyl stearate. Also preferred are isopropyl myristate, isopropyl palmitate, isopropyl stearate, isopropyl isostearate, isopropyl oleate, isooctyl stearate, Isononylstearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, diisotridecylacetate, n-butyl stearate, n-hexyl laurate, n-decyl oleate and oleyl oleate.

Further cosmetic oils preferred as contemplated herein are selected from natural and synthetic hydrocarbons, particularly preferably from mineral oils, paraffin oils, $C_{18}$-$C_{30}$ isoparaffins, in particular isoeicosane, polyisobutenes and polydecenes, which are known, for example, under the name Emery® 3004, 3006, 3010 or under the name Ethylflo® from Albemarle® or Nexbase® 2004G, further selected from $C_8$-$C_{16}$ isoparaffins, in particular from isodecane, isododecane, isotetradecane and isohexadecane and mixtures thereof, and 1,3-di-(2-ethylhexyl) cyclohexane.

Further cosmetic oils preferred as contemplated herein are selected from the benzoic acid esters of linear or branched C8-22 alkanols. C12-C15-alkyl benzoate, isostearyl benzoate, ethylhexyl benzoate and octyl docecyl benzoate are particularly preferred.

Other preferred oils as contemplated herein are selected from fatty alcohols with 6-30 carbon atoms, which are unsaturated or branched and saturated or branched and unsaturated. The branched alcohols are often referred to as Guerbet alcohols. Preferred alcohol oils are 2-octyldodecanol, 2-hexyldecanol, 2-ethylhexyl alcohol and isostearyl alcohol. 2-octyldodecanol is especially preferred.

Further cosmetic oils preferred as contemplated herein are selected from the triglycerides (i. e. triple esters of glycerol)

of linear or branched, saturated or unsaturated, optionally hydroxylated C8-30 fatty acids. The use of natural oils, e.g. Amaranth seed oil, apricot kernel oil, argan oil, avocado oil, babassu oil, cottonseed oil, borage seed oil, camelina oil, safflower oil, peanut oil, pomegranate seed oil, hemp oil, hazelnut oil, elderberry seed oil, currant seed oil, jojoba oil, linseed oil, macadamia nut oil, corn oil, almond oil, marula oil, evening primrose oil, olive oil, palm oil, palm kernel oil, Brazil nut oil, pecan nut oil, peach kernel oil, rapeseed oil, castor oil, sea buckthorn pulp oil, sea buckthorn kernel oil, sesame oil, soybean oil, sunshine flower oil, grape seed oil, walnut oil, wild rose oil, wheat germ oil, and the liquid components of coconut oil and the like. However, synthetic triglyceride oils, in particular cosmetic oils with the INCI denomination "capric/caprylic triglycerides", are also preferred.

Further cosmetic oils which are particularly preferred as contemplated herein are selected from the dicarboxylic acid esters of linear or branched C2-C10 alkanols, diisopropyl adipate, di-n-butyl adipate, di-(2-ethylhexyl) adipate, dioctyl adipate, dioctyl malate, dioctyl maleate, dicaprylyl maleate, diisooctyl succinate, di-2-ethylhexyl succinate and di-(2-hexyldecyl) succinate.

Further cosmetic oils which are suitable as contemplated herein are selected from the silicone oils, to which e.g., dialkyl- and alkylarylsiloxanes, such as cyclopentasiloxane, cyclohexasiloxane, dimethylpolysiloxane and methylphenylpolysiloxane, but also hexamethyldisiloxane, octamethyltrisiloxane and decamethyltetrasiloxane count. Preferred can be volatile silicone oils, which can be cyclic, such as octamethylcyclotetrasiloxane, decamethylcyclopentasiloxane and dodecamethylcyclohexasiloxane, as well as mixtures thereof. Also suitable are volatile linear silicone oils, hexamethyldisiloxane ($L_2$), octamethyltrisiloxane ($L_3$), decamethyltetrasiloxane ($L_4$) and any two- and three-component mixtures of $L_2$, $L_3$ and/or $L_4$, preferably mixtures such as those described, for. B. in the commercial products DC 2-1184, Dow Corning® 200 (0.65 cSt) and Dow Corning® 200 (1.5 cSt) from Dow Corning. Preferred non-volatile silicone fluids are selected from higher molecular weight linear dimethylpolysiloxanes, with kinematic viscosities (25° C.) in the range of 5 to 100 cSt, preferably 5 to 50 cSt or even 5 to 10 cSt, and dimethylpolysiloxane with a kinematic viscosity (25° C.) of about 350 cSt.

As contemplated herein, it can be extremely preferred to use mixtures of the oils.

Preferred dyeing agent according to the invention are characterized in that they contain at least one cosmetic oil, which is selected from natural and synthetic hydrocarbons, particularly preferably mineral oils, $C_{18}$-$C_{30}$ isoparaffins, especially isoeicosane, polyisobutenes, polydecenes, and $C_8$-$C_{16}$ isoparaffins; fatty alcohols containing 6-30 carbon atoms that are unsaturated or branched and saturated or branched and unsaturated; triglycerides of linear or branched, saturated or unsaturated, optionally hydroxylated $C_{8-30}$ fatty acids, in particular natural oils; the esters of linear or branched saturated or unsaturated fatty alcohols having 2-30 carbon atoms with linear or branched, saturated or unsaturated fatty acids having 2-30 carbon atoms, which may be hydroxylated; the $C_8$-$C_{22}$ fatty alcohol esters of monovalent or polyvalent $C_2$-$C_7$ hydroxycarboxylic acids; silicone oils and mixtures of the aforementioned substances.

Further preferred dyeing agents according to the invention are characterized in that they contain water, in each case based on their weight, in an amount of from about 30 to about 95% by weight, preferably from about 40 to about 90% by weight, further preferably from about 50 to about 80% by weight and more preferably from about 60 to about 70% by weight.

Furthermore, preferred dyeing agent according to the invention may contain additional active ingredients, auxiliaries and additives, such as thickening agents, hair-conditioning agents, antioxidants in order to improve the shelf-stability of the oxidation-sensitive dye precursors against premature oxidation during storage, sequestrants and organic solvents.

Suitable thickening agents may be selected from natural polymers, especially polysaccharides, like cellulose, cellulose esters and cellulose ethers, xanthan gums, guar gums or scleroglucan gums. Further suitable thickening agents may be selected from synthetic polymers, especially acrylate-based polymers and copolymers and acryloyldimethyltaurate-based polymers. Suitable hair-conditioning agents may be selected from polymers, especially from cationic and amphoteric polymers, like polyquaternium-4, polyquaternium-6, polyquaternium-7, polyquaternium-10, polyquaternium-16, polyquaternium-22, polyquaternium-37, polyquaternium-39 and, preferably, polyquaternium-53. Preferred agents for oxidative dyeing according to the invention are characterized in that they comprise at least one polyquaternium, in each case based on their weight, in an amount of from about 0.01% to about 3% by weight, preferably from about 0.05% to about 2% by weight, more preferably from about 0.1% to about 1% by weight, even more preferably from about 0.2% to about 0.7% by weight, most preferably from about 0.4% to about 0.5% by weight.

Polyquaternium-53, which is a highly preferred conditioning agent according to the present invention, can improve the intensity of the hair coloration. Polymers with the INCI denomination "polyquaternium-53" are amphoteric terpolymers, consisting essentially of the monomers acrylic acid (anionic), acrylamide (nonionic) and methacrylamidopropyltrimethyl ammonium chloride (cationic). Preferred agents for oxidative dyeing according to the invention are characterized in that they comprise polyquaternium-53, in each case based on their weight, in an amount of from about 0.01% to about 3% by weight, preferably from about 0.05% to about 2% by weight, more preferably from about 0.1% to about 1% by weight, even more preferably from about 0.2% to about 0.7% by weight, most preferably from about 0.4% to about 0.5% by weight.

Further hair-conditioning agents are selected from amino acids, oligopeptides, protein hydrolysates and proteins, waxes and butters, as well as mixtures thereof.

If the dyeing agent according to the invention shall be applied as a foam or spray, it may contain propellants such as propane, butanes, pentanes or isopentanes, $N_2O$, dimethyl ether, $CO_2$ and/or pressurized air.

To prepare the ready-to-use dyeing mixture and to initiate the dye formation reaction, the dyeing agent according to the invention, being component (C1) of the dyeing kit, is mixed with a second component (C2), being an aqueous hydrogen peroxide-containing composition with acidic pH. The obtained ready-to-use dyeing mixture is intended for immediate application to the hair to be dyed.

To avoid incompatibilities and prevent premature, undesirable dye formation, components (C1) (containing the oxidation dye precursors) and (C2) (acidic aqueous oxidant preparation with hydrogen peroxide) are always packaged separately and brought into contact with each other only shortly before use. For the consumer, the components (C1) and (C2) are preferably provided in the form of a multi-component packaging unit (kit-of-parts).

A second object of the present disclosure is therefore a multi-component kit-of-parts for oxidative dyeing of keratinous fibers, in particular human hair, comprising at least two separately prepared components (C1) and (C2), wherein
the first component (C1) is an agent according to the invention or preferred embodiments of the invention, being free or substantially free of dissolved hydrogen peroxide, comprising
(A) the coupling oxidation dye precursor 2-(1,3-benzodioxol-5-ylamino)ethanol and/or at least one of its physiologically tolerated salts, and
(B) the coupling oxidation dye precursor 1-phenyl-3-methylpyrazol-5-one and/or at
least one of its physiologically tolerated salts, and
(C) at least one oxidation dye precursor of the oxidation base-type,
the second component (C2) is an aqueous hydrogen peroxide-containing composition with acidic pH.

Components (C1) and (C2) can be mixed in different weight ratios (C1)/(C2) of, for example, from about 0.3 to about 3.0, preferably from about 0.5 to about 2.5, particularly preferably from about 0.45 to about 1.5, and exceptionally preferably in a weight ratio of about 1:1.

In addition, the multi-component packaging units as contemplated herein may also contain one or more further separately assembled components. This or these additional separately prepared components may be, for example, a pre-treatment agent or an aftertreatment agent, such as shampoos or conditioners.

A further object of the present disclosure is a process for the oxidative hair dyeing of keratinous fibers, in particular human hair, in which an agent according to the invention or according to preferred embodiments of the invention is mixed with an acidic aqueous hydrogen peroxide-containing composition and directly afterwards applied to the fibers, in particular the hair, is left there on the fibers for a time of from 1 to 60 minutes, preferably from 20 to 45 minutes, at room temperature and/or at least 30° C., the fibers, in particular the hair, are then rinsed with water and/or a cleansing composition and, if desired, an aftertreatment agent is applied to the fibers, in particular the hair, which is optionally rinsed out, and the hair is then dried.

As contemplated herein, the term "room temperature" denotes the temperature in the room in which a person usually uses a hair dye, usually a bathroom or a hairdressing salon, where a temperature in the range from about 10-29° C. prevails.

Leaving the hair dyeing ready-to-use mixture on the fibers, in particular the hair, can also be done at least at about 30° C., preferably at about 30-60° C., particularly preferably at about 32-50° C., if the hair is heated, for example, with a heat hood or with a radiant heater.

The oxidizing agent preparation (C2) used in dyeing kits as contemplated herein and in dyeing processes preferred as contemplated herein contains, in each case based on its weight, preferably from about 40 to about 96% by weight, particularly preferably from about 70 to about 93% by weight, exceptionally preferably from about 80 to about 90% by weight, of water.

The oxidizing agent preparation (C2) used in dyeing kits as contemplated herein and in dyeing processes as contemplated herein further contains, in each case based on its weight, preferably about 0.5 to about 23% by weight, further preferably from about 2.5 to about 21% by weight, particularly preferably from about 4 to about 20% by weight, most preferably from about 5 to about 18% by weight and exceptionally preferably from about 6 to about 12% by weight, of hydrogen peroxide.

To stabilize the hydrogen peroxide, the acidic aqueous oxidant preparation (C2) preferably has a pH in the range from about 2.0 to about 6.5, particularly preferably from about 2.5 to about 5.5, exceptionally preferably from about 2.8 to about 5.0, in each case measured at 20° C.

The acidic aqueous oxidant preparations (C2) used as contemplated herein and preferably used as contemplated herein may also contain stabilizers, especially sequestrants resp. complexing agents, and pH buffer substances.

In a further preferred embodiment of the present disclosure, the oxidizing agent preparation (C2) used as contemplated herein contains at least one cosmetic oil in a total amount of about 0.2 to about 50% by weight, preferably from about 2 to about 40% by weight, particularly preferably from about 8 to about 30% by weight, extremely preferably from about 15 to about 25% by weight, in each case based on the weight of the oxidizing agent preparation (C2).

The at least one cosmetic oil present in the oxidizer preparation (C2) in a total amount of about 0.2 to about 50 wt. %, based on the weight of the preparation (C2), is preferably selected from natural and synthetic hydrocarbons, particularly preferably from mineral oil, paraffin oils, $C_{18}$-$C_{30}$ isoparaffins, in particular isoeicosane, polyisobutenes and polydecenes, and $C_8$-$C_{16}$ isoparaffins, triglycerides of linear or branched, saturated or unsaturated, optionally hydroxylated $C_{8-30}$ fatty acids, especially natural oils; the dicarboxylic acid esters of linear or branched $C_2$-$C_{10}$ alkanols; the esters of linear or branched, saturated or unsaturated fatty alcohols having 2-30 carbon atoms with linear or branched, saturated or unsaturated fatty acids having 2-30 carbon atoms which may be hydroxylated; silicone oils and mixtures of the aforementioned substances. Oils particularly preferred in this connection as contemplated herein are selected from paraffin oils and the esters of linear or branched saturated or unsaturated fatty alcohols having 2-30 carbon atoms with linear or branched saturated or unsaturated fatty acids having 2-30 carbon atoms, which may be hydroxylated, and mixtures thereof; extremely preferably selected from paraffin oil, isopropyl palmitate and isopropyl myristate and mixtures thereof.

In a further preferred embodiment of the present disclosure, the oxidizing agent preparation (C2) used as contemplated herein contains at least one surfactant selected from anionic surfactants and non-ionic surfactants and mixtures thereof in a total amount of about 0.05 to about 2 wt. %, preferably from about 0.3 to about 1.5 wt. %, of the oxidizing agent preparation (C2), and at least one linear, saturated 1-alcanol having 14 to 22 carbon atoms, selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of about 1 to about 5% by weight, preferably from about 1.5 to about 4% by weight, all the quantitative data being based on the weight of the oxidizing agent preparation (C2).

A further kit-of-parts preferred as contemplated herein and a further hair dyeing process preferred as contemplated herein are each exemplified in that the oxidant preparation (C2) comprises at least one surfactant selected from anionic surfactants and non-ionic surfactants and mixtures thereof in a total amount of about 0.05 to about 2% by weight, preferably from about 0.3 to about 1.5% by weight, and at least one linear, saturated 1-alcanol having 14 to 22 carbon atoms, selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of about 1 to about 5% by weight, preferably from about 1.5 to about 4% by weight, in each case based on the weight of the oxidant preparation (C2).

In summary, the subject-matters of the present invention can be characterized by the following points:

1. An agent for the oxidative dyeing of keratinous fibers, in particular human hair, which contains
   (A) the coupling oxidation dye precursor 2-(1,3-benzodioxol-5-ylamino)ethanol and/or at least one of its physiologically tolerated salts, and
   (B) the coupling oxidation dye precursor 1-phenyl-3-methylpyrazol-5-one and/or at least one of its physiologically tolerated salts, and
   (C) at least one oxidation dye precursor of the oxidation base-type,
   wherein the agent is further substantially free of dissolved hydrogen peroxide.
2. The agent according to point 1, characterized in that it comprises the oxidation dye precursor 2-(1,3-benzodioxol-5-ylamino)ethanol and/or at least one of its physiologically tolerated salts in a total amount of 0.01 to 5.0% by weight, preferably 0.03 to 3.0% by weight, particularly preferably 0.05 to 1.5% by weight, the amounts being based on the weight of the agent.
3. The agent according to point 1 or 2, characterized in that it comprises the coupling oxidation dye precursor 1-phenyl-3-methylpyrazol-5-one and/or at least one of its physiologically tolerated salts in a total amount of 0.01 to 1.0% by weight, preferably 0.05 to 0.5% by weight, particularly preferably 0.08 to 0.2% by weight, the amounts being based on the weight of the agent.
4. The agent according to any one of points 1 to 3, characterized in that the at least one oxidation base (C) is selected from para-phenylenediamine, toluene-2,5-diamine, 2-methoxymethyl-para-phenylenediamine, 2-(2,5-diaminophenyl)ethanol, N,N-bis-(2-hydroxyethyl)-p-phenylenediamine, 4-amino-3-methylphenol, 4-aminophenol, 4,5-diamino-1-(2-hydroxyethyl)-1H-pyrazole, 2-(1,2-dihydroxyethyl)-p-phenylenediamine, N,N'-bis-(2-hydroxyethyl)-N,N'-bis-(4-aminophenyl)-1,3-diamino-propane-2-ol, bis-(2-hydroxy-5-aminophenyl) methane, 1,3-bis-(2,5-diaminophenoxy)-propane-2-ol, N,N'-bis-(4-aminophenyl)-1,4-diazacycloheptane, 1,10-bis-(2,5-diaminophenyl)-1,4,7,10-tetraoxadecane, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo-[1,2-a]-pyrazole-1-one and their physiologically tolerated salts as well as mixtures of the aforementioned substances, preferably selected from para-phenylenediamine, toluene-2,5-diamine, 2-methoxymethyl-para-phenylenediamine, 2-(2,5-diaminophenyl)ethanol, N,N-bis-(2-hydroxyethyl)-p-phenylenediamine, 4-amino-3-methylphenol, 4-aminophenol, 4,5-diamino-1-(2-hydroxyethyl)-1H-pyrazole, and their physiologically tolerated salts as well as mixtures of the aforementioned substances.
5. The agent according to any one of points 1 to 4, characterized in that the at least one oxidation base and/or at least one of its physiologically tolerated salts is contained in a total amount of 0.001 to 5.0% by weight, preferably 0.01 to 3.0% by weight, particularly preferably 0.05 to 1.5% by weight, the amounts being based on the weight of the agent.
6. The agent according to any one of points 1 to 5, characterized in that it comprises at least one additional coupling oxidation dye precursor and/or at least one of its physiologically tolerated salts in a total amount of 0.001 to 5.0% by weight, preferably 0.01 to 3.0% by weight, particularly preferably 0.05 to 1.5% by weight, the amounts being based on the weight of the agent.
7. The agent according to any one of points 1 to 6, characterized in that the at least one additional coupling oxidation dye precursor is selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 1,3-phenylenediamine, 2-(2,4-diaminophenoxy)ethanol, 1-methoxy-2-amino-4-(2-hydroxyethylamino)benzene, 1,3-bis(2,4-diaminophenoxy)propane, 1,3-bis(2,4-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 3-amino-4-(2-methoxyethoxy)-5-methylphenylamine, 1-amino-3-bis-(2-hydroxyethyl)aminobenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-naphthol, 1,5-dihydroxynaphthalene, 2,7-dihydroxynaphthalene, 1,7-dihydroxynaphthalene, 1,8-dihydroxynaphthalene, 2-methylresorcinol, 4-chlororesorcinol, 4-hydroxyindole, 6-hydroxyindole, 7-hydroxyindole, 4-hydroxyindoline, 6-hydroxyindoline and/or 7-hydroxyindoline and their physiologically tolerated salts as well as mixtures of the aforementioned substances.
8. The agent according to any one of points 1 to 7, characterized in that the at least one additional coupling oxidation dye precursor is selected from 3-aminophenol, 5-amino-2-methylphenol, 2-amino-3-hydroxypyridine, 2-(2,4-diaminophenoxy)ethanol, 1-naphthol, 1-methoxy-2-amino-4-(2-hydroxy-ethylamino)benzene, 1,3-bis(2,4-diaminophenoxy)propane, 3-amino-2-methylamino-6-methoxypyridine, 2,7-dihydroxynaphthalene and their physiologically tolerated salts as well as mixtures of the aforementioned substances, more preferably selected from 3-aminophenol, 5-amino-2-methylphenol, 2-amino-3-hydroxypyridine, 2-(2,4-diaminophenoxy)ethanol and 1-naphthol, their physiologically tolerated salts as well as mixtures of the aforementioned substances.
9. The agent according to any one of points 1 to 8, characterized in that it is substantially free of resorcinol (1,3-dihydroxybenzene).
10. The agent according to any one of points 1 to 9, characterized in that it is substantially free of any resorcinol compound of structure (I)

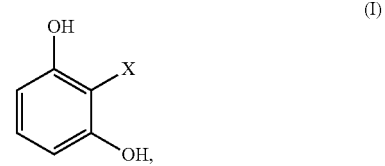

in which

X means a hydrogen atom or a C1-C10 alkyl group, preferably a hydrogen atom or a methyl group.

11. The agent according to any one of points 1 to 10, characterized in that it is substantially free of any resorcinol compound of structure (II)

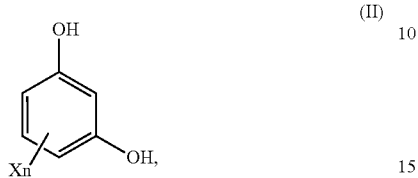

(II)

in which

X means a chlorine atom or a C1-C10 alkyl group and n means an integer from zero to 4.

12. The agent according to any one of points 1 to 11, characterized in that it comprises polyquaternium-53, preferably in an amount of from about 0.01% to about 3% by weight, more preferably from about 0.05% to about 2% by weight, even more preferably from about 0.1% to about 1% by weight, even more preferably from about 0.2% to about 0.7% by weight, most preferably from about 0.4% to about 0.5% by weight, in each case based on the weight of the agent.

13. The agent according to any one of points 1 to 12, characterized in that it comprises a dye precursor mixture, which consists essentially of one of the following combinations, using the free bases or their physiologically tolerated salts:

- 2-(1,3-benzodioxol-5-ylamino)ethanol, 1-phenyl-3-methylpyrazol-5-one, 3-aminophenol and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diaminophenyl)ethanol and mixtures of the aforementioned oxidation bases;
- 2-(1,3-benzodioxol-5-ylamino)ethanol, 1-phenyl-3-methylpyrazol-5-one, 3-aminophenol, 5-amino-2-methylphenol and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diaminophenyl)ethanol and mixtures of the aforementioned oxidation bases;
- 2-(1,3-benzodioxol-5-ylamino)ethanol, 1-phenyl-3-methylpyrazol-5-one, 3-aminophenol, 5-amino-2-methylphenol, 2,4-diaminophenoxyethanol and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diamino-phenyl)ethanol and mixtures of the aforementioned oxidation bases;
- 2-(1,3-benzodioxol-5-ylamino)ethanol, 1-phenyl-3-methylpyrazol-5-one, 3-aminophenol, 2,4-diaminophenoxyethanol and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diaminophenyl)ethanol and mixtures of the aforementioned oxidation bases;
- 2-(1,3-benzodioxol-5-ylamino)ethanol, 1-phenyl-3-methylpyrazol-5-one, 3-aminophenol, 2,4-diaminophenoxyethanol, 2-amino-3-hydroxypyridine, and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diaminophenyl)ethanol and mixtures of the aforementioned oxidation bases;
- 2-(1,3-benzodioxol-5-ylamino)ethanol, 1-phenyl-3-methylpyrazol-5-one, 3-aminophenol, 2-amino-3-hydroxypyridine, and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diaminophenyl)ethanol and mixtures of the aforementioned oxidation bases;
- 2-(1,3-benzodioxol-5-ylamino)ethanol, 1-phenyl-3-methylpyrazol-5-one, 3-aminophenol, 2-amino-3-hydroxypyridine, 1-naphthol, and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diamino-phenyl)ethanol and mixtures of the aforementioned oxidation bases;
- 2-(1,3-benzodioxol-5-ylamino)ethanol, 1-phenyl-3-methylpyrazol-5-one, 3-aminophenol, para-phenylenediamine, N,N-bis-(2-hydroxyethyl)-p-phenylenediamine, 4-amino-3-methylphenol and 4-aminophenol;
- 2-(1,3-benzodioxol-5-ylamino)ethanol, 1-phenyl-3-methylpyrazol-5-one, 3-aminophenol, 5-amino-2-methylphenol, para-phenylenediamine, N,N-bis-(2-hydroxyethyl)-p-phenylenediamine, 4-amino-3-methylphenol and 4-aminophenol;
- 2-(1,3-benzodioxol-5-ylamino)ethanol, 1-phenyl-3-methylpyrazol-5-one, 3-aminophenol, 5-amino-2-methylphenol, 2,4-diaminophenoxyethanol, para-phenylenediamine, N,N-bis-(2-hydroxyethyl)-p-phenylenediamine, 4-amino-3-methylphenol and 4-aminophenol;
- 2-(1,3-benzodioxol-5-ylamino)ethanol, 1-phenyl-3-methylpyrazol-5-one, 3-aminophenol, 2,4-diaminophenoxyethanol, para-phenylenediamine, N,N-bis-(2-hydroxyethyl)-p-phenylenediamine, 4-amino-3-methylphenol and 4-aminophenol;
- 2-(1,3-benzodioxol-5-ylamino)ethanol, 1-phenyl-3-methylpyrazol-5-one, 3-aminophenol, 2,4-diaminophenoxyethanol, 2-amino-3-hydroxypyridine, para-phenylenediamine, N,N-bis-(2-hydroxyethyl)-p-phenylenediamine, 4-amino-3-methylphenol and 4-aminophenol;
- 2-(1,3-benzodioxol-5-ylamino)ethanol, 1-phenyl-3-methylpyrazol-5-one, 3-aminophenol, 2-amino-3-hydroxypyridine, para-phenylenediamine, N,N-bis-(2-hydroxyethyl)-p-phenylenediamine, 4-amino-3-methylphenol and 4-aminophenol;
- 2-(1,3-benzodioxol-5-ylamino)ethanol, 1-phenyl-3-methylpyrazol-5-one, 3-aminophenol, 2-amino-3-hydroxypyridine, 1-naphthol, para-phenylenediamine, N,N-bis-(2-hydroxyethyl)-p-phenylenediamine, 4-amino-3-methylphenol and 4-aminophenol.

14. A multicomponent kit-of-parts for oxidative dyeing of keratinous fibers, in particular human hair, comprising at least two separately packaged components (C1) and (C2), wherein
the first component (C1) according to any of the points 1 to 13, being substantially free of dissolved hydrogen peroxide, comprising
   (A) the coupling oxidation dye precursor 2-(1,3-benzodioxol-5-ylamino)ethanol and/or at least one of its physiologically tolerated salts, and
   (B) the coupling oxidation dye precursor 1-phenyl-3-methylpyrazol-5-one and/or at least one of its physiologically tolerated salts, and
   (C) at least one oxidation dye precursor of the oxidation base-type,
the second component (C2) is an aqueous hydrogen peroxide-containing composition with acidic pH.

15. A process for the oxidative hair dyeing of keratinous fibers, in particular human hair, in which an agent according to one of Points 1 to 13 is mixed with an acidic, aqueous hydrogen peroxide-containing composition and directly afterwards applied to the fibers, in particular the hair, is left there on the fibers for a time of from 1 to 60 minutes, preferably from 20 to 45 minutes, at room temperature and/or at least 30° C., the fibers, in particular the hair, are then rinsed with water and/or a cleansing composition and, if desired, an aftertreatment agent is applied to the fibers, in particular the hair, which is optionally rinsed out, and the hair is then dried.

The following examples are intended to illustrate the subject matter of the present disclosure without limiting it herein.

EXAMPLES

Production of Dyeing Agents

The following color creams were produced (all figures are in percent by weight unless otherwise stated):

TABLE 1 color cream (component (C1))

| Ingredient INCI Names | WEIGHT % |
|---|---|
| Propylene Glycol | 2%-3% |
| Sodium Sulfite | 0.1%-1% |
| Erythorbic Acid | 0.1%-1% |
| EDTA | 0.1%-1% |
| L-Arginine | 0.1%-2% |
| Sodium Metasilicate | 0.1%-1% |
| Cetearyl Alcohol | 0.1%-5% |
| Cetyl Alcohol | 0.1%-5% |
| Stearic Acid | 0.1%-2% |
| Glyceryl Stearate | 0.1%-2% |
| Steareth-21 | 0.1%-5% |
| Glycol distearate | 0.1%-2% |
| Stearamidopropyl dimethylamine | 0.1%-5% |
| Mineral Oil | 0.1%-2% |
| Isostearic acid | 0.1%-2% |
| Polysorbate 80 | 0.1%-2% |
| Polyquaternium 53 | 0.1%-5% |
| Fragrance | 0.1%-2% |
| Dye Powder Formula | Indicated in table 3 |
| Ammonium hydroxide (28% solution) | 1%-12% |
| Water | q.s to 100 |

TABLE 2 oxidizing agent (component (C2))

| Ingredient INCI names | Weight % |
|---|---|
| Hydrogen peroxide | 3%-15% |
| Methylparaben | 0.1%-1% |
| Cetearyl alcohol | 0.1%-2% |
| Mineral oil | 0.1%-2% |
| Ceteth-20 | 0.1%-2% |
| Acrylates/Ceteth-20 Itaconate Copolymer | 0.02%-1% |
| Sodium Lauryl Sulfate | 0.02%-0.5% |
| Phosphoric Acid | 0.02%-0.5% |
| Disodium Phosphate | 0.01%-1% |
| Sodium Stannate | 0.01%-1% |
| Squalane | 0.01%-1% |
| Water | q.s to 100 |

TABLE 3

Dye Powder Formulas (comparative (with resorcinol)) and (inventive (without resorcinol) (all quantities in weight-%, referring to the total weight of the agent for the oxidative dyeing including the cream base, without hydrogen peroxide)

| INCI Name | 5N [wt.-%] | 5N no RES [wt.-%] | 6NG [wt.-%] | 6NG no RES [wt.-%] | 5NA [wt.-%] | 5NA no RES [wt.-%] | 5BA [wt.-%] | 5BA no RES [wt.-%] |
|---|---|---|---|---|---|---|---|---|
| p-Phenylenediamine | 0.4 | 0.35 | 0.29 | 0.29 | 0.44 | 0.2 | 0.17 | 0.17 |
| p-Aminophenol | 0.053 | 0.15 | 0.46 | 0.46 | — | 0.15 | 0.008 | 0.008 |
| N,N-bis-(2-hydroxy-ethyl)-p-phenylenediamine sulfate | 0.45 | 0.45 | 0.064 | 0.064 | 0.132 | 0.45 | 0.075 | 0.075 |
| 4-amino-3-methylphenol (4-amino-m-cresol) | — | 0.5 | — | 0.5 | — | 0.15 | — | 0.06 |
| Resorcinol | 0.683 | — | 0.45 | — | 0.502 | — | 0.215 | — |
| 2-Methylresorcinol | 0.088 | — | 0.128 | — | — | — | — | — |
| m-Aminophenol | 0.106 | 0.1 | 0.245 | 0.25 | — | 0.1 | 0.022 | 0.022 |

TABLE 3-continued

Dye Powder Formulas (comparative (with resorcinol)) and (inventive (without resorcinol) (all quantities in weight-%, referring to the total weight of the agent for the oxidative dyeing including the cream base, without hydrogen peroxide)

| INCI Name | 5N [wt.-%] | 5N no RES [wt.-%] | 6NG [wt.-%] | 6NG no RES [wt.-%] | 5NA [wt.-%] | 5NA no RES [wt.-%] | 5BA [wt.-%] | 5BA no RES [wt.-%] |
|---|---|---|---|---|---|---|---|---|
| Hydroxyethyl-3,4-Methylenedioxyaniline HCl | — | 0.5 | — | 0.3 | — | 0.45 | — | 0.2 |
| 2-Amino-3-hydroxy-pyridine | — | — | — | 0.1 | — | 0.1 | 0.005 | 0.005 |
| 4-Amino-2-hydroxy-toluene | — | 0.1 | — | — | — | — | — | — |
| 2,4-Diaminophenoxyethanol HCl | 0.011 | 0.01 | — | — | 0.031 | 0.01 | 0.075 | 0.075 |
| 1-Naphthol | — | — | 0.018 | 0.02 | — | — | — | — |
| 1-Phenyl-3-methyl-5-pyrazolone | 0.14 | 0.18 | 0.18 | 0.18 | 0.088 | 0.18 | 0.055 | 0.18 |

TABLE 4

Colorimetric results
L.A.B Spectrophotometer readings of control shades with resorcinol and resorcinol derivates vs. resorcinol free shade matching

| | L*(D65) | a*(D65) | b*(D65) | dL*(D65) | da*(D65) | db*(D65) | dE*ab(D65) |
|---|---|---|---|---|---|---|---|
| 5N | 24.48 | 2.78 | 6.92 | — | — | — | — |
| 5N no RES | 24.60 | 2.09 | 7.24 | 0.12 | −0.69 | 0.32 | 0.77 |
| 6NG | 26.73 | 5.42 | 9.83 | — | — | — | — |
| 6NG no RES | 26.23 | 4.89 | 7.41 | −0.5 | −0.52 | −2.43 | 2.53 |
| 5NA | 27.72 | 2.47 | 7.11 | — | — | — | — |
| 5NA no RES | 26.73 | 2.76 | 8.41 | 2.44 | 0.29 | 1.3 | 2.78 |
| 5BA | 28.72 | 1.16 | 1.73 | — | — | — | — |
| 5BA no RES | 27.18 | 0.05 | 3.62 | −1.54 | −1.11 | 1.89 | 2.68 |

Ready-to-use oxidative hair coloring agents were prepared by first mixing each color cream according to table 1 in combination with the dye mixture according to table 3, resulting in a component (C1), then mixing component (C1) and the oxidizing agent component (C2) according to table 2 in equal parts by weight (1:1).

Oxidative Dyeing of the Keratin Fibers

Natural white hair strands were treated as follows.

One of each of the 8 ready-to-use oxidative hair coloring agents was applied to the hair strands immediately after its preparation (liquor ratio 4 grams of ready-to-use colorant per gram of hair) and left on the hair for an exposure time of 30 minutes at room temperature (22° C.). The dye was then rinsed out of the strands with water. The strands were first dried with a towel and then in a stream of cold air.

Colorimetric Measurements

All hair strands were colorimetrically measured at four different measuring points along the strand before and after dyeing. Color measurements were carried out according to the L*a*b* color system.

Three hair strands were used for each of the colorants from #1 to #12 and the arithmetic mean of each measured L*a*b* value was calculated for all hair strands.

The mean values for the L*a*b* values are noted in table 4.

The dE values being below 3.0 means the shade is a closer match.

The comparison between the results of the colorimetric measurements in table 4 shows that substituting resorcinol by different oxidation bases and coupling dye precursors cannot easily be done. Appropriate oxidation bases/coupler combinations have to be selected carefully in order to match the shade of the resorcinol Control shades (benchmark).

TABLE 5

Shade matching for shade 5N
(All quantities in weight-%, referring to the total weight of the agent for the oxidative dyeing including the cream base, without hydrogen peroxide)

| INCI Name | Control 5N | Trial 1 | Trial 2 | Trial 3 | Trial 4 | Trial 5 | Trial 6 (Final) |
|---|---|---|---|---|---|---|---|
| p-phenylenediamine | 0.4 | 0.35 |  | 0.35 | 0.35 | 0.35 | 0.35 |
| toluene-2,5-diamine sulfate | — | 0 | 0.55 | 0 | 0 | 0 | 0 |
| p-Aminophenol | 0.053 | 0.053 | 0.053 | 0.053 | 0.053 | 0.15 | 0.15 |
| N,N-bis-(2-hydroxy-ethyl)-p-phenylene-diamine sulfate | 0.45 | 0.45 | 0.5 | 0.45 | 0.45 | 0.45 | 0.45 |
| Resorcinol | 0.683 | 0 | 0 | 0 | 0 | 0 | 0 |
| 2-Methylresorcinol | 0.088 | 0 | 0 | 0 | 0 | 0 | 0 |
| m-Amino-phenol | 0.106 | 0.1 | 0.1 | 0.2 | 0 | 0.1 | 0.1 |
| 4-amino-3-methyl-phenol (4-amino-m-cresol) |  | 0.5 | 0.5 | 0.5 | 0.5 | 0.5 | 0.45 |
| Hydroxyethyl-3,4-methylenedioxy-aniline HCl |  | 0 | 0 | 0 | 0.5 | 0.5 | 0.35 |
| 2-Amino-3-hydroxy-pyridine |  | 0 | 0 | 0 | 0 | 0 | 0 |
| 4-Amino-2-hydroxy-toluene |  | 0 | 0 | 0 | 0 | 0 | 0.1 |
| 2,4-Diaminophen-oxyethanol HCl | 0.011 | 0.011 | 0.011 | 0 | 0 | 0.01 | 0.01 |
| 1-Naphthol |  | 0.042 | 0.042 | 0 | 0 | 0 | 0 |
| 1-Phenyl-3-methyl-5-pyrazolone | 0.14 | 0 | 0 | 0 | 0 | 0.17 | 0.17 |
| Observation compared to the Control 5N |  | too red | too red | too mahogany red | green | green brown | Matched - more neutral than control |

The best color match results from the dye combination hydroxyethyl-3,4-methylenedioxyaniline HCl with 1-phenyl-3-methyl-5-pyrazolone.

What is claimed is:

1. An agent for the oxidative dyeing of keratinous fibers, comprising:
   (A) a coupling oxidation dye precursor 2-(1,3-benzodioxol-5-ylamino) ethanol and/or at least one of its physiologically tolerated salts, and
   (B) a coupling oxidation dye precursor 1-phenyl-3-methylpyrazol-5-one and/or at least one of its physiologically tolerated salts, and
   (C) at least one oxidation dye precursor, said oxidation dye precursor being an oxidation base-type,
   wherein the agent is substantially free of any resorcinol compound of structure (1)

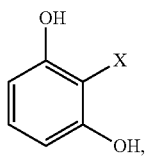
(1)

in which X means a hydrogen atom or a C1-C10 alkyl group,
wherein the agent is substantially free of dissolved hydrogen peroxide.

2. The agent according to claim 1, wherein the coupling oxidation dye precursor 2-(1,3-benzodioxol-5-ylamino) ethanol and/or at least one of its physiologically tolerated salts comprises 0.01 wt % to 5.0 wt % based on the total weight of the agent.

3. The agent according to claim 1, wherein the coupling oxidation dye precursor 2-(1,3-benzodioxol-5-ylamino) ethanol and/or at least one of its physiologically tolerated salts comprises 0.05 wt % to 1.5 wt % based on the total weight of the agent.

4. The agent according to claim 1, wherein the coupling oxidation dye precursor 1-phenyl-3-methylpyrazol-5-one and/or at least one of its physiologically tolerated salts comprises 0.01 wt % to 1.0 wt % based on the total weight of the agent.

5. The agent according to claim 1, wherein the coupling oxidation dye precursor 1-phenyl-3-methylpyrazol-5-one and/or at least one of its physiologically tolerated salts comprises 0.08 wt % to 0.2 wt % based on the total weight of the agent.

6. The agent according to claim 1, wherein the at least one oxidation base is selected from the group consisting of: para-phenylenediamine, toluene-2,5-diamine, 2-methoxymethyl-para-phenylenediamine, 2-(2,5-diamino-phenyl) ethanol, N,N-bis-(2-hydroxyethyl)-p-phenylenediamine, 4-amino-3-methylphenol, 4-aminophenol, 4,5-diamino-1-(2-hydroxyethyl)-1H-pyrazole, 2-(1,2-dihydroxyethyl)-p-phenylenediamine, N,N'-bis-(2-hydroxyethyl)-N,N'-bis-(4-aminophenyl)-1,3-diamino-propane-2-ol, bis-(2-hydroxy-5-aminophenyl) methane, 1,3-bis-(2,5-diaminophenoxy)-propane-2-ol, N,N'-bis-(4-aminophenyl)-1,4- diazacycloheptane, 1,10-bis-(2,5-diaminophenyl)-1,4,7,10-tetraoxadecane, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo-[1,2-a]-pyrazole-1-one and their physiologically tolerated salts and mixtures of the aforementioned substances, their physiologically tolerated salts, and mixtures thereof.

7. The agent according to claim 1, wherein the at least one oxidation base is selected from the group consisting of: para-phenylenediamine, toluene-2,5-diamine, 2-methoxymethyl-para-phenylenediamine, 2-(2,5-diamino-phenyl) ethanol, N,N-bis-(2-hydroxyethyl)-p-phenylenediamine, 4-amino-3-methylphenol, 4-aminophenol, 4,5-diamino-1-(2-hydroxyethyl)-1H-pyrazole, their physiologically tolerated salts, and mixtures thereof.

8. The agent according to claim 1, wherein the at least one oxidation base and/or at least one of its physiologically tolerated salts is present comprises 0.001 wt % to 5.0 wt % based on the total weight of the agent.

9. The agent according to claim 1, wherein the at least one oxidation base and/or at least one of its physiologically tolerated salts is present comprises 0.05 wt % to 1.5 wt % based on the total weight of the agent.

10. The agent according to claim 1, wherein the agent further comprises at least one additional coupling oxidation dye precursor and/or at least one of its physiologically tolerated salts in an amount of 0.001 wt % to 5.0 wt % based on the total weight of the agent.

11. The agent according to claim 10, wherein the at least one additional coupling oxidation dye precursor is selected from the group consisting of: 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 1,3-phenylenediamine, 2-(2,4-diaminophenoxy) ethanol, 1-methoxy-2-amino-4-(2-hydroxyethylamino) benzene, 1,3-bis (2,4-diaminophenoxy) propane, 1,3-bis (2,4-diaminophenyl) propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl) amino]-4,5-dimethylphenyl} amino) ethanol, 3-amino-4-(2-methoxyethoxy)-5methylphenylamine, 1-amino-3-bis-(2-hydroxyethyl) aminobenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-naphthol, 1,5-dihydroxynaphthalene, 2,7-dihydroxynaphthalene, 1,7-dihydroxynaphthalene, 1,8-dihydroxynaphthalene, 2-methylresorcinol, 4-chlororesorcinol, 4-hydroxy-indole, 6-hydroxyindole, 7-hydroxyindole, 4-hydroxyindoline, 6-hydroxyindoline and/or 7-hydroxyindoline, their physiologically tolerated salts, and mixtures thereof.

12. The agent according to claim 10, wherein the at least one additional coupling oxidation dye precursor is selected from the group consisting of: 3-aminophenol, 5-amino-2-methylphenol, 2-amino-3-hydroxypyridine, 2-(2,4-diaminophenoxy) ethanol, 1-naphthol, 1-methoxy-2-amino-4-(2-hydroxy-ethylamino) benzene, 1,3-bis (2,4-diaminophenoxy) propane, 3-amino-2-methylamino-6-methoxypyridine, 2,7-dihydroxynaphthalene and their physiologically tolerated salts and mixtures of the aforementioned substances.

13. The agent according to claim 1, wherein the agent further comprises polyquaternium-53.

14. The agent according to claim 13, wherein the polyquaternium-53 is present in an amount of about 0.01 wt % to about 3 wt % based on the total weight of the agent.

15. The agent according to claim 1, wherein the agent comprises a dye precursor mixture, which consists essentially of one of the following combinations, using the free bases or their physiologically tolerated salts:
2-(1,3-benzodioxol-5-ylamino) ethanol, 1-phenyl-3-methylpyrazol-5-one, 3-aminophenol and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diaminophenyl) ethanol and mixtures of the aforementioned oxidation bases;
2-(1,3-benzodioxol-5-ylamino) ethanol, 1-phenyl-3-methylpyrazol-5-one, 3-aminophenol, 5-amino-2-methylphenol and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diaminophenyl) ethanol and mixtures of the aforementioned oxidation bases;
2-(1,3-benzodioxol-5-ylamino) ethanol, 1-phenyl-3-methylpyrazol-5-one, 3-aminophenol, 5-amino-2-methylphenol, 2,4-diaminophenoxyethanol and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diamino-phenyl) ethanol and mixtures of the aforementioned oxidation bases;
2-(1,3-benzodioxol-5-ylamino) ethanol, 1-phenyl-3-methylpyrazol-5-one, 3-aminophenol, 2,4-diaminophenoxyethanol and at least one of the oxidation bases para-phenylenediamine, N, N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diaminophenyl) ethanol and mixtures of the aforementioned oxidation bases;
2-(1,3-benzodioxol-5-ylamino) ethanol, 1-phenyl-3-methylpyrazol-5-one, 3-aminophenol, 2,4-diaminophenoxyethanol, 2-amino-3-hydroxypyridine, and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diamino-phenyl) ethanol and mixtures of the aforementioned oxidation bases;
2-(1,3-benzodioxol-5-ylamino) ethanol, 1-phenyl-3-methylpyrazol-5-one, 3-aminophenol, 2-amino-3-hydroxypyridine, and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diaminophenyl) ethanol and mixtures of the aforementioned oxidation bases;
2-(1,3-benzodioxol-5-ylamino) ethanol, 1-phenyl-3-methylpyrazol-5-one, 3-aminophenol, 2-amino-3-hydroxypyridine, 1-naphthol, and at least one of the oxidation bases para-phenylenediamine, N,N-bis-(2-hydroxyethyl)-p-phenylenediamine, 4-amino-3-methylphenol, 4-aminophenol, toluene-2,5-diamine, 2-methoxymethyl-para-phenylenediamine, 2-(2,5-diamino-phenyl) ethanol and mixtures of the aforementioned oxidation bases;

2-(1,3-benzodioxol-5-ylamino) ethanol, 1-phenyl-3-methylpyrazol-5-one, 3-aminophenol, para-phenylenediamine, N,N-bis-(2-hydroxyethyl)-p-phenylene-diamine, 4-amino-3-methylphenol and 4-aminophenol;

2-(1,3-benzodioxol-5-ylamino) ethanol, 1-phenyl-3-methylpyrazol-5-one, 3-aminophenol, 5-amino-2-methylphenol, para-phenylenediamine, N,N-bis-(2-hydroxyethyl)-p-phenylenediamine, 4-amino-3-methylphenol and 4-aminophenol;

2-(1,3-benzodioxol-5-ylamino) ethanol, 1-phenyl-3-methylpyrazol-5-one, 3-aminophenol, 5-amino-2-methylphenol, 2,4-diaminophenoxyethanol, para-phenylenediamine, N,N-bis-(2-hydroxyethyl)-p-phenylenediamine, 4-amino-3-methylphenol and 4-aminophenol;

2-(1,3-benzodioxol-5-ylamino) ethanol, 1-phenyl-3-methylpyrazol-5-one, 3-aminophenol, 2,4-diaminophenoxyethanol, para-phenylenediamine, N,N-bis-(2-hydroxyethyl)-p-phenylenediamine, 4-amino-3-methylphenol and 4-aminophenol;

2-(1,3-benzodioxol-5-ylamino) ethanol, 1-phenyl-3-methylpyrazol-5-one, 3-aminophenol, 2,4-diaminophenoxyethanol, 2-amino-3-hydroxypyridine, para-phenylenediamine, N,N-bis-(2-hydroxyethyl)-p-phenylenediamine, 4-amino-3-methylphenol and 4-aminophenol;

2-(1,3-benzodioxol-5-ylamino) ethanol, 1-phenyl-3-methylpyrazol-5-one, 3-aminophenol, 2-amino-3-hydroxypyridine, para-phenylenediamine, N,N-bis-(2-hydroxyethyl)-p-phenylenediamine, 4-amino-3-methylphenol and 4-aminophenol; or 2-(1,3-benzodioxol-5-ylamino) ethanol, 1-phenyl-3-methylpyrazol-5-one, 3-aminophenol, 2-amino-3-hydroxypyridine, 1-naphthol, para-phenylenediamine, N,N-bis-(2-hydroxyethyl)-p-phenylenediamine, 4-amino-3-methylphenol and 4-aminophenol.

16. A multicomponent kit-of-parts for oxidative dyeing of keratinous fibers, comprising at least two separately packaged components (C1) and (C2), wherein the first component (C1) is substantially free of dissolved hydrogen peroxide, and comprises:
(A) the coupling oxidation dye precursor 2-(1,3-benzodioxol-5-ylamino) ethanol and/or at least one of its physiologically tolerated salts, and
(B) the coupling oxidation dye precursor 1-phenyl-3-methylpyrazol-5-one and/or at least one of its physiologically tolerated salts, and
(C) at least one oxidation dye precursor of the oxidation base-type, the second component (C2) is an aqueous hydrogen peroxide-containing composition with acidic pH wherein all components of the kit are free of any resorcinol compound of structure (1)

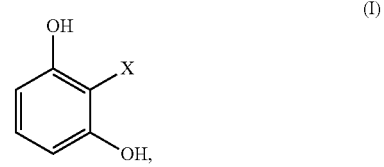
(I)

in which X means a hydrogen atom or a C1-C10 alkyl group.

17. A process for the oxidative hair dyeing of keratinous fibers, comprising mixing an agent in accordance with claim 1 and an aqueous hydrogen peroxide-containing composition,
directly applying to keratinous fibers,
leaving on the keratinous fibers for a time of from 1 to 60 minutes at room temperature or higher, rinsing the keratinous fibers with water and/or a cleansing composition,
optionally, applying an aftertreatment agent to the keratinous fibers.

* * * * *